United States Patent
Kitajo et al.

(10) Patent No.: US 11,630,512 B2
(45) Date of Patent: Apr. 18, 2023

(54) DETERMINATION DEVICE, DETERMINATION METHOD, PROGRAM, AND INFORMATION STORAGE MEDIUM

(71) Applicant: RIKEN, Saitama (JP)

(72) Inventors: Keiichi Kitajo, Saitama (JP); Hiromichi Suetani, Oita (JP)

(73) Assignee: RIKEN, Saitama (JP)

( * ) Notice: Subject to any disclaimer, the term of this patent is extended or adjusted under 35 U.S.C. 154(b) by 1444 days.

(21) Appl. No.: 15/576,632

(22) PCT Filed: May 27, 2016

(86) PCT No.: PCT/JP2016/065789
§ 371 (c)(1),
(2) Date: Jul. 31, 2018

(87) PCT Pub. No.: WO2016/190428
PCT Pub. Date: Dec. 1, 2016

(65) Prior Publication Data
US 2019/0025918 A1 Jan. 24, 2019

(30) Foreign Application Priority Data
May 28, 2015 (JP) .............................. JP2015-108664

(51) Int. Cl.
*A61B 5/377* (2021.01)
*A61B 5/117* (2016.01)
(Continued)

(52) U.S. Cl.
CPC .............. *G06F 3/015* (2013.01); *A61B 5/117* (2013.01); *A61B 5/369* (2021.01); *A61B 5/377* (2021.01);
(Continued)

(58) Field of Classification Search
None
See application file for complete search history.

(56) References Cited

U.S. PATENT DOCUMENTS

| 2006/0241382 A1 | 10/2006 | Li et al. |
| 2009/0222305 A1* | 9/2009 | Berg, Jr. ............ G06Q 30/0201 |
| | | 705/7.29 |

(Continued)

FOREIGN PATENT DOCUMENTS

| JP | 2004-248714 | 9/2004 |
| WO | 2014178323 | 11/2014 |

OTHER PUBLICATIONS

Kitajo et al., "Consistency of human brain response to noisy visual inputs", 2014 International Symposium on Nonlinear Theory and its Applications, NOLTA2014, Luzern, Switzerland, p. 443-445, Sep. 14-18, 2014.

(Continued)

*Primary Examiner* — Thaddeus B Cox
*Assistant Examiner* — Marc D. Honrath
(74) *Attorney, Agent, or Firm* — Ohlandt, Greeley, Ruggiero and Perle, LLP

(57) ABSTRACT

In each trial, brain electrical activity at multiple points of a target person is measured. An acquirer of a determination device acquires response matrices for n trials under a first condition and response matrices form trials under a second condition. An analyzer performs canonical correlation analysis on the acquired response matrices to obtain first canonical variable time series. A distance calculator calculates a distance between the trials from the obtained first canonical variable time series to obtain a distance matrix. A determiner obtains a possibility that the n trials and the m trials are classified into two different clusters from the distance matrix and determines whether the first condition and the second condition are substantially different. It is (Continued)

possible to provide to a single target person a first content in n trials and a second content in m trials so as to determine a difference in interest of the single target person. It is possible to provide the same content to a first subject who is the target person in n trials and to a second subject who is the target person in m trials so as to determine whether the two are different or the same.

12 Claims, 14 Drawing Sheets

(51) Int. Cl.
    *A61B 5/369*     (2021.01)
    *G06F 18/231*     (2023.01)
    *G06F 17/15*     (2006.01)
    *G06F 3/01*     (2006.01)
    *A61B 5/00*     (2006.01)
    *A61M 21/00*     (2006.01)

(52) U.S. Cl.
    CPC .............. *A61B 5/40* (2013.01); *A61B 5/4064* (2013.01); *G06F 17/15* (2013.01); *G06F 18/231* (2023.01); *A61M 2021/005* (2013.01); *A61M 2021/0027* (2013.01); *G06F 2203/011* (2013.01)

(56) References Cited

U.S. PATENT DOCUMENTS

| | | | |
|---|---|---|---|
| 2010/0063368 A1* | 3/2010 | Leuthardt | G16H 20/10 600/27 |
| 2015/0045654 A1* | 2/2015 | Lee | A61B 5/055 600/413 |
| 2015/0080753 A1* | 3/2015 | Miyazaki | G11B 27/031 386/230 |
| 2015/0095101 A1* | 4/2015 | Kymal | G06F 30/00 705/7.28 |
| 2015/0119745 A1* | 4/2015 | Similowski | A61M 16/026 600/544 |
| 2015/0272461 A1 | 10/2015 | Morimoto et al. | |

OTHER PUBLICATIONS

International Search Report dated Aug. 30, 2016 from corresponding PCT International Application No. PCT/JP2016/065789, 3 pages.

\* cited by examiner

Pop music

Classical music

DETERMINATION DEVICE, DETERMINATION METHOD, PROGRAM, AND INFORMATION STORAGE MEDIUM

TECHNICAL FIELD

The present disclosure relates to a determination device determining the presence/absence of substantial difference in trial condition such as the subject being different/the same or the presence/absence of difference in interest of the subject in an object by measuring the brain waves, a determination method, a program for realizing them by a computer, and a non-transitory computer-readable information recording medium on which the program is recorded.

BACKGROUND ART

In the prior art, biometric authentication techniques for performing authentication based on features of a living body have been proposed. In such biometric authentication, whether the person is different/the same is determined by observing unchanging external features of a person such as fingerprints, iris forms, the facial shape or externally observing a specific conscious behavior of a person such as voiceprint.

On the other hand, Patent Literature 1 proposes a technique of acquiring brain waves of a candidate at measuring points, saving in a database frequency components of the brain waves of the candidate, acquiring brain waves of an authentication target person at the measuring points, acquiring frequency components of the brain waves of the authentication target person, calculating the distances between the frequency components by, for example, the Euclidean distance, and authenticating the identicalness between the candidate and the authentication target person depending on their closeness.

On the other hand, research by the inventors of the present application revealed presence of consistency of the brain activity when a person is shown a visual stimulus of a noise time series of the same actual value (Non Patent Literature 1).

CITATION LIST

Patent Literature

Patent Literature 1: Unexamined Japanese Patent Application Kokai Publication No. 2004-248714.

Non Patent Literature

Non Patent Literature 1: Keiichi Kitajo and Hiromichi Suetani, Consistency of human brain response to noisy visual inputs, 2014 International Symposium on Nonlinear Theory and its Applications, NOLTA 2014, Luzern, Switzerland, p. 443-445, Sep. 14-18, 2014.

SUMMARY OF INVENTION

Technical Problem

Research by the inventors of the present application revealed that since the human brain waves behave nonlinearly and the human brain waves significantly change depending on the type and content of an external stimulus, sufficient accuracy is not obtained in determining whether the person is different/the same based on the distances between frequency components of brain waves. Thus, it is practically impossible to determine whether the subject is different/the same using the technique disclosed in the Patent Literature 1.

Then, there is a demand for a new technique of determining whether the subject is different/the same by measuring the brain waves.

Furthermore, there is a strong demand for application of the principle of the technique to determining whether there is a difference in trial condition by measuring the brain waves. In other words, in addition to determining whether the subject is different/the same, there is a strong demand for performing on a subject trials with respect to each of multiple objects and determining whether there is a difference in interest in the multiple objects and further determining the magnitude relationship of the degrees of interest in the multiple objects.

The present disclosure is intended to solve the above problem and an objective of the disclosure is to provide a determination device that determines the presence/absence of substantial difference in trial condition such as the subject being different/the same or the presence/absence of difference in interest of the subject in an object by measuring the brain waves, a determination method, a program for realizing them by a computer, and a non-transitory computer-readable information recording medium storing the program.

Solution to Problem

The present disclosure relates to a determination device and a determination method executed by the determination device, and the determination device acquires (n+m) response matrices by measuring brain electrical activity of a target person in n trials under a first condition and m trials under a second condition;

performs canonical correlation analysis on response matrices included in the acquired (n+m) response matrices to obtain first canonical variable time series for the response matrices;

calculates a distance between the trials for the response matrices from the obtained first canonical variable time series; and obtains a possibility that the n trials and the m trials are classified into two different clusters from the calculated distance and determines whether the first condition and the second condition are substantially different based on the possibility.

Advantageous Effects of Invention

The present disclosure can provide a determination device determining the presence/absence of substantial difference in trial condition such as the subject being different/the same or the presence/absence of difference in interest of the subject in an object by measuring the brain waves, a determination method, a program for realizing them by a computer, and a non-transitory computer-readable information recording medium storing the program.

DESCRIPTION OF EMBODIMENTS

Figure 1:
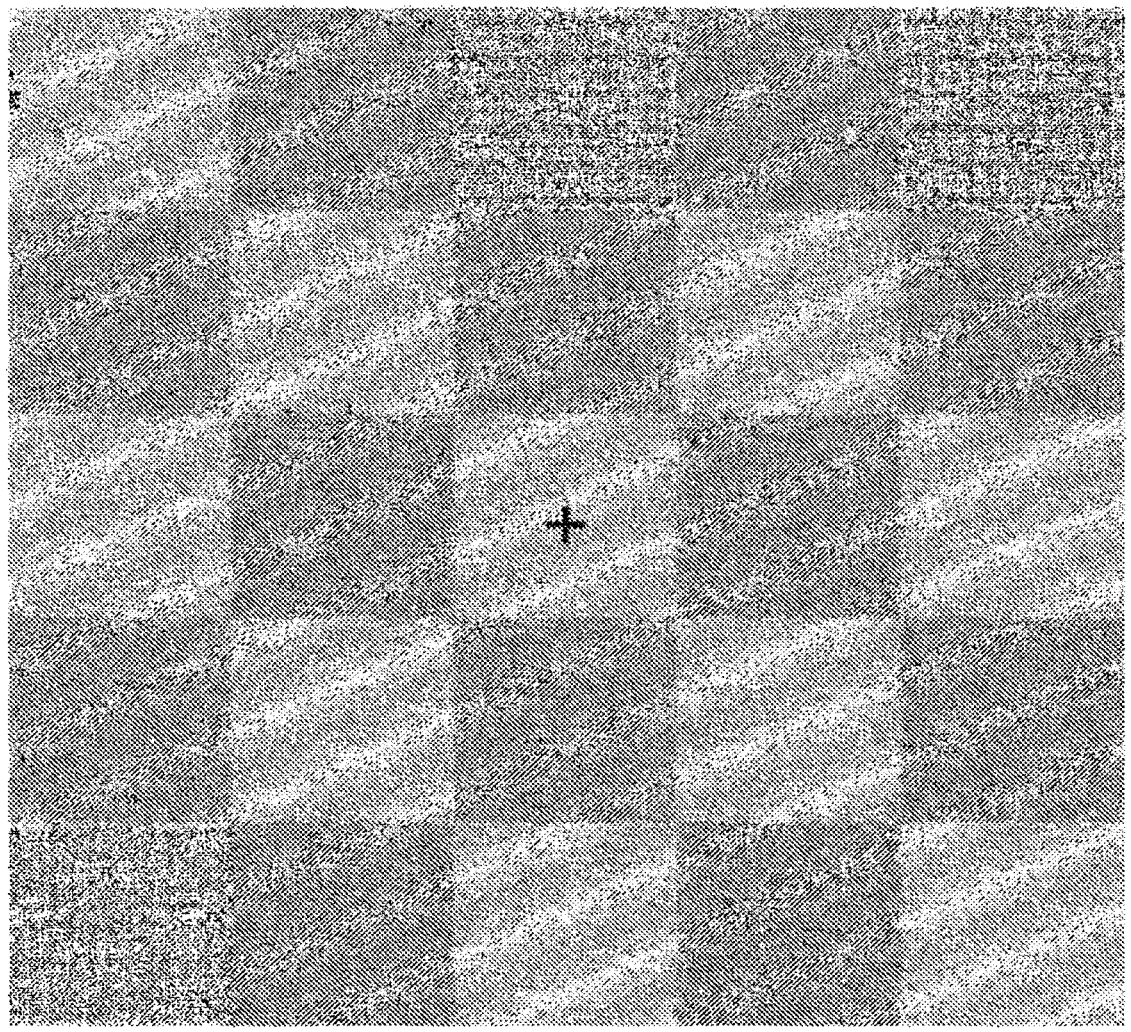
FIG. 1 is an explanatory illustration showing an example of the random video according to a practical example of the present disclosure.

An embodiment of the present disclosure will be described below. Here, this embodiment is given for the purpose of explanation and does not confine the scope of the present disclosure. Therefore, a person in the field can adopt an embodiment in which some or all elements of this embodiment are replaced with those equivalent thereto. Moreover, the elements described in each practical example can be omitted as appropriate depending on the intended use. As just stated, any embodiment configured according to the principle of the present disclosure is included in the scope of the present disclosure.

(Basic Configuration)

In this embodiment, on the premise that n trials are performed under a first condition and m trials are performed under a second condition on a target person so that the brain activity of the target person is measured in a total of (n+m) trials, the determination device acquires (n+m) response matrices obtained in the measurement.

Then, the determination device performs canonical correlation analysis on response matrices included in the (n+m) response matrices to obtain first canonical variable time series of the response matrices.

Then, the determination device calculates the distance between the trials for the response matrices from the obtained first canonical variable time series.

Furthermore, the determination device obtains the possibility that the n trials under the first condition and the m trials under the second condition are classified into two different clusters from the determined distance and determines whether the first condition and the second condition are substantially different based on the possibility.

A combination of a first condition and a second condition can be that, for example, a target person observes or listens to two different contents. In this mode, it is determined whether there is a difference in interest of the target person in the two contents or things indicated by the two contents, in other words whether the target person distinguishes the two. Therefore, in this mode, preference of the target person to the contents or the things can be examined.

Besides, it is applicable to the situation in which the target person who observes or listens to the same content may be the same or may be different under the first condition and under the second condition. In such a case, it is determined whether the target person of n trials under a first condition (a first subject) and the target person of m trials under a second condition (a second subject) are different individuals or the same individual. Thus, in this mode, the determination device can function as an authentication device for authenticating an individual.

First, a typical mode for the determination device to function as an authentication device will be described below. Then, various modes for implementing the present disclosure will be described.

(Trials and Authentication with a Random Video)

A mode for the determination device to determine whether a subject is different/the same so as to authenticate the subject will be described below. In this embodiment, on a target subject, multiple trials are performed at the time of user registration and multiple trials are performed at the time of authentication. In other words, in this practical example, a target person of trials is assumed to be a trial condition, and the authentication is performed based on whether the subject is different at the time of registration and at the time of authentication.

Details of trials will be described below.

In the trials of this embodiment, a subject observes a predetermined same random video.

FIG. 1 is an explanatory illustration showing an example of the random video according to a practical example of the present disclosure. This figure shows a frame of a random video in which the contrast between dark squares and bright squares of a gray checkerboard pattern of five squares x five squares is randomly changed. In this random video, a black cross line attracting the attention of the subject is rendered at the center.

This random video comprises monoclonal images in which the white pixel value is 255 and the black pixel value is 0. The average brightness of all squares of the checkerboard is 128 and the pixel values of all dark squares and all bright squares are changed at a time randomly according to the Gaussian distribution with a proper standard deviation such as a standard deviation of 2, 4, 6, 8, 10, or the like. The frequency of change is 30 times per second (30 fps) and the total length of the random video is eight seconds.

As the random video used for authentication, once decided to use, the same one is used in all trials. In the above example, constants common to all trials are used as seeds of pseudo random numbers for changing the contrast randomly.

As the random video, in addition to the above example, a noisy video that is difficult for a person to consciously read its intension such as a white noise video, a pink noise video, a Brownian noise video, and a gray noise video can be used as appropriate.

The random video may be reproduced successively or intermittently with another video in-between. Another video reproduced between the random video can be a noisy video of a different configuration.

In each trial, the brain electrical activity of the subject is continuously measured at multiple points while the subject observes the random video. Typically, using an electroencephalograph having the appearance of a cap with scalp electrodes making contact with multiple points on the scalp of the subject, the scalp potential is measured 1000 times per second and measurements on 63 channels are obtained. In this practical example, since an eight-second long random video is used, 63 time series of measurements of 8000 in length are obtained in one trial.

However, the number of measuring points can be changed as appropriate. Moreover, the brain surface may invasively be measured as the measurement points. Moreover, as the brain electrical activity to measure, other than the potential, the electrode contact resistance may be measured, or the magnetic field occurring near the scalp along with the electrical activity of nerve cells may be measured.

In the following explanation, multiple trials at the time of user registration are termed trials $1, 2, \ldots, n$ and multiple trials at the time of authentication are termed trial $n+1, n+2, \ldots, n+m$. A subject of trials $1, 2, \ldots, n$ is termed a registering user or a first subject. A subject of trials $n+1, n+2, \ldots, n+m$ is termed a target user or a second subject. The number of trials at the time of registration, n, and the number of trials at the time of authentication, m, can be changed as appropriate. However, in this practical example, it is assumed that $n=m=10$ or $n=m=5$.

Here, the trials $1, 2, \ldots, n$ are performed all together only one time at the time of registration for authentication of a user (a first subject). Therefore, after the user registration is completed, the value of n does not change.

On the other hand, the trials $n+1, n+2, \ldots, n+m$ are performed each time a user attempts the authentication. The authentication target user may be the same as or different from the first subject. Moreover, measurement environments change at each authentication. Thus, it may be possible to discard trials results under poor measurement environments and change the value of m at each authentication.

(Hardware for Realizing the Determination Device)

The determination device according to this embodiment is typically realized by a computer executing a program. The computer is connected to input devices such as an electroencephalograph and transmits/receives information to/from such devices.

The program executed by the computer can be distributed/sold by a server communicably connected to the computer. Additionally, it is possible to store the program on a non-transitory information recording medium such as a compact disk read only memory (CD-ROM), a flash memory, and an electrically erasable programmable ROM (EEPROM) and distribute/sell the non-transitory information recording medium.

The program is installed on a non-transitory information recording medium such as a hard disk, a solid state drive, a flash memory, or an EEPROM possessed by the computer. Then, the information processing device in this embodiment is realized by the computer. Generally, the central processing unit (CPU) of a computer reads a program from a non-transitory information recording medium to a random access memory (RAM) and interprets and executes the codes included in the program under the control of an operating system (OS) of the computer. However, with an architecture enabling mapping of a non-transitory information recording medium in a memory space accessible by the CPU, explicit loading of a program onto the RAM may sometimes be unnecessary. Here, various kinds of information necessary in the process of executing a program can temporarily be stored in the RAM.

Instead of realizing the information processing device of this embodiment by a general-purpose computer, the information processing device of this embodiment can be configured by a dedicated electronic circuit. In this mode, the program can be used as a material for creating a wiring chart, a timing chart, or the like of an electronic circuit. In such a mode, an electronic circuit fulfilling the specification prescribed in the program is configured by a field programmable gate array (FPGA) or an application specific integrated circuit (ASIC) and the electronic circuit functions as a dedicated device fulfilling the function prescribed in the program and realizes the information processing device of this embodiment.

For easier understanding, the following explanation will be made on the premise of a mode in which the determination device is realized by a computer executing a program.

(Configuration of the Determination Device)

Figure 2:
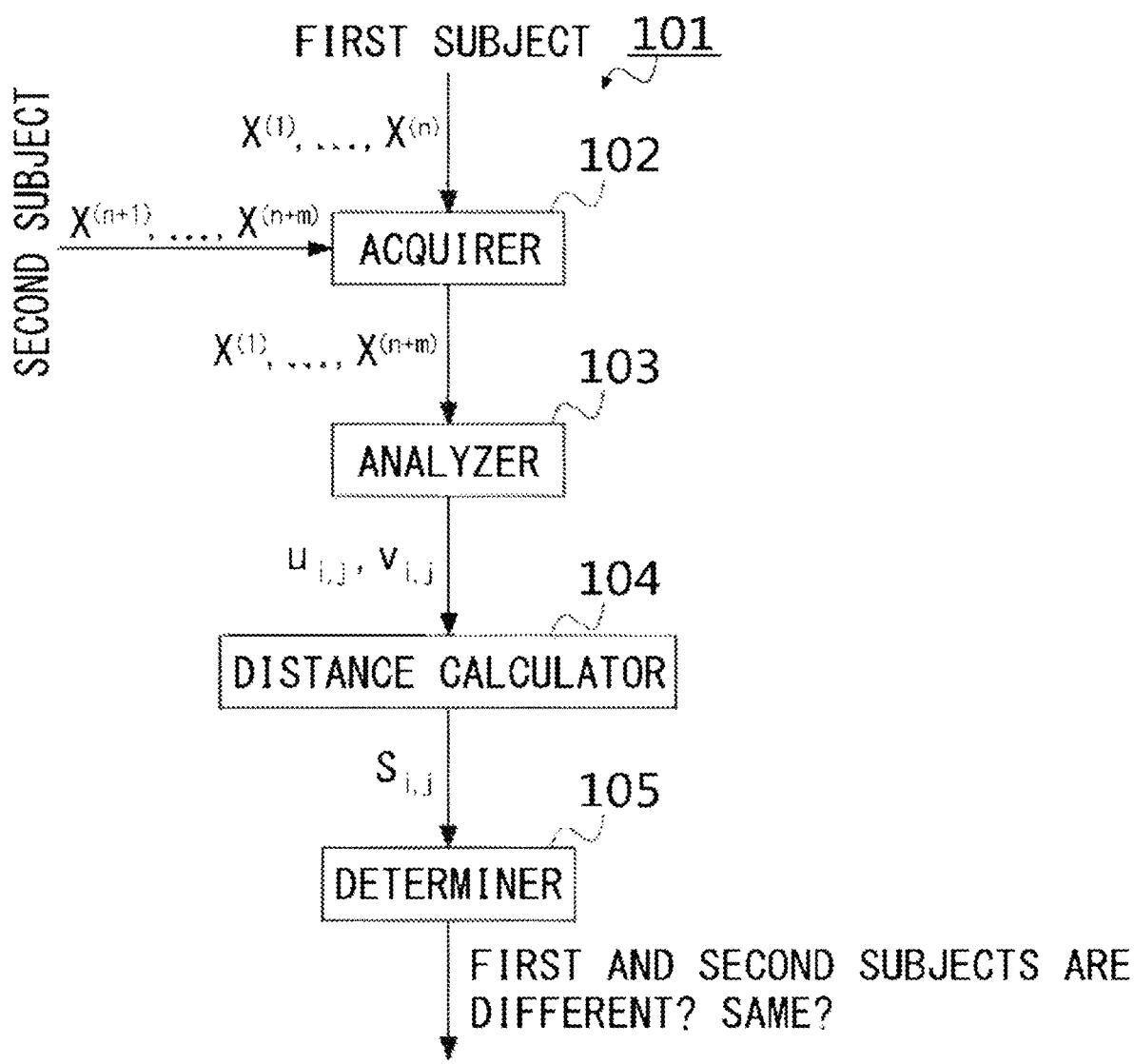
FIG. 2 is an explanatory chart showing the general configuration of the determination device according to the practical example of the present disclosure.

FIG. 2 is an explanatory chart showing the general configuration of the determination device according to the practical example of the present disclosure. As shown in this figure, a determination apparatus 101 comprises an acquirer 102, an analyzer 103, a distance calculator 104, and a determiner 105. The functions of the parts are realized by a computer executing code fragments included in a program and associated with the parts.

Here, the acquirer 102 acquires (1) response matrices $X^{(1)}, X^{(2)}, \ldots, X^{(n)}$ in respective trials $1, 2, \ldots, n$ performed on a first subject, and (2) response matrices $X^{(n+1)}, X^{(n+2)}, \ldots, X^{(n+m)}$ in respective trials $n+1, n+2, \ldots, n+m$ performed on a second subject.

As described above, the brain electrical activity at D points of the first subject is measured T times while the first subject observes a predetermined random video in each of trials $1, 2, \ldots, n$, and the brain electrical activity at D points of the second subject is measured T times while the second subject observes the predetermined random video in each of trials $n+1, n+2, \ldots, n+m$. In the above-described setting example, $D=63$ and $T=8000$. Here, it is possible to eliminate a beginning part and an end part of the video observation so that, for example, $T=7000$.

Moreover, the elements of the response matrices $X^{(1)}, X^{(2)}, \ldots, X^{(n)}$ and $X^{(n+1)}, X^{(n+2)}, \ldots, X^{(n+m)}$ are set as follows. In other words, for each of an integer i ($i=1, 2, \ldots, n, n+1, n+2, \ldots, n+m$), an integer p ($p=1, 2, \ldots, D$), and an integer t ($t=1, 2, \ldots, T$), an element $X^{(i)}_p(t)$ in a row p and a column t of a response matrix $X^{(i)}$ obtained in a trial i has a value measured at a p-th point among the D points at a t-th sampling time since random video observation starts.

Here, as the measurements included in the response matrices $X^{(1)}, X^{(2)}, \ldots, X^{(n)}$ and the response matrices $X^{(n+1)}, X^{(n+2)}, \ldots, X^{(n+m)}$, the potentials measured with the electrodes or the like may be used as they are or may properly be normalized. For example, normalization based on the amplitudes of elements of a matrix or normalization by application of a frequency filter can be performed.

Here, as the amplitudes of elements of a matrix, the maximum value of absolute values of matrix elements, the mean square value of matrix elements, the means square value of matrix elements plus the standard deviation of matrix elements multiplied by a constant, or the like can be used. Then, the elements of the matrix are scaler-multiplied so that the amplitude is a constant such as 1.

Additionally, a bandpass filter transmitting, for example, a bandwidth from 2 Hz to 100 Hz can be applied to the rows of a response matrix as a frequency filter for removing various kinds of noise and artifacts.

Furthermore, it is possible to apply a normalization technique in electroencephalography for removing various kinds of noise and artifacts from the brain waves Furthermore, the above-described normalization may be applied in combination. The normalization can be performed before the analyzer 103 performs canonical correlation analysis.

Next, the analyzer 103 performs canonical correlation analysis on the response matrix $X^{(i)}$ and the response matrix $X^{(j)}$ for each of the integer i (i=1, 2, . . . , n, n+1, n+2, . . . , n+m) and the integer j (j=1, 2, . . . , n, n+1, n+2, . . . , n+m) to obtain a first canonical variable time series $u_{i,j}$ for the response matrix $X^{(i)}$ and a first canonical variable time series $v_{i,j}$ for the response matrix $X^{(j)}$.

Here, generally, canonical correlation analysis is performed to obtain scaler time series u and v and vector time series ξ and η satisfying a condition regarding given correlation coefficients from vector time series x and y. The values at a time t of the vector time series x and y, the scaler time series u and v and the vector time series ξ and η are denoted by vectors x(t) and y(t), scalars u(t) and v(t), and vectors ξ(t) and η(t). The scalar time series u and v are also termed first canonical variable time series.

The vector time series can be expressed by a matrix. In other words, a vector at a certain time is expressed by a column vector and a vector at a time t is placed in a t-th column. Then, the above response matrix $X^{(i)}$ is interpreted as a vector time series.

In canonical correlation analysis, the above satisfies the following relationship expressed by the inner product of vectors. In other words, at a time t, $u(t) = \langle x(t), \xi(t) \rangle$; and $v(t) = \langle y(t), \eta(t) \rangle$.

The vector time series ξ and η are so selected to maximize the correlation coefficient of the first canonical variable time series u and v. Here, the correction coefficient R(u, v) is calculated from the covariance and the standard deviation in the direction of time as follows:

$R(u,v) = \text{cov}(u,v)/(\sigma(u) \times \sigma(v))$.

Here, generally, the average and the standard deviation of the scalar time series u and v and the covariance of the scalar time series u and v are defined as follows on the premise that a time t is included in a range from 1 to T:

$\text{mean}(u) = (1/T) \times \Sigma_{t=1}^{T} u(t)$;

$\sigma(u)^2 = (1/T) \times \Sigma_{t=1}^{T} [u(t) - \text{mean}(u)]^2$; and $\text{cov}(u,v) = (1/T) \times \Sigma_{t=1}^{T} [u - \text{mean}(u)] \times [v(t) - \text{mean}(v)]$.

The canonical correlation analysis can be considered to be a maximization problem to obtain the vector time series ξ and η that maximize the correlation coefficient R(u, v). This problem results in a generalized eigenvalue problem. However, for extracting nonlinear information, for example, techniques using the kernel method and the regularization method in combination and the like are widely used. Therefore, with application of those various kinds of known techniques, the first canonical variable time series $u_{i,j}$ for the response matrix $X^{(i)}$ and the first canonical variable time series $v_{i,j}$ for the response matrix $X^{(j)}$ can be obtained by performing canonical correlation analysis on the response matrix $X^{(i)}$ and the response matrix $X^{(j)}$.

Then, the distance calculator 104 calculates a distance matrix S. Here, for each of the integer i (i=1, 2, . . . , n, n+1, n+2, . . . , n+m) and the integer j (j=1, 2, . . . , n, n+1, n+2, . . . , n+m), an element $S_{i,j}$ in a row i and a column j of a distance matrix S is the distance between a trial i and a trial j. The element $S_{i,j}$ is calculated from the first canonical variable time series $u_{i,j}$ and the first canonical variable time series $v_{i,j}$.

Here, the following can be used as the distance d(u, v) calculated from the time series u and v.

First, the Euclidean distance defined by the square root of square sum of differences at times t can be used:

$s(u,v) = [\Sigma_{t=1}^{T} (u(t) - v(t))^2]^{1/2}$.

Alternatively, the mean square of differences may be used:

$s(u,v) = [(1/T) \times \Sigma_{t=1}^{T} (u(t) - v(t))^2]^{1/2}$.

Next, the Manhattan distance defined by the sum of the absolute values of differences at times t can be used:

$s(u,v) = \Sigma_{t=1}^{T} |u(t) - v(t)|$.

Alternatively, the mean of the absolute values of differences may be used:

$s(u,v) = (1/T) \times \Sigma_{t=1}^{T} |u(t) - v(t)|$.

Additionally, the cosine similarity may be used, in which assuming that u and v are T-dimensional vectors, the distance is determined from the cosine of the angle between the two.

Once trials 1, 2, . . . , n on a first subject are finished, the distances between the trials 1, 2, . . . , n can be calculated even before trials n+1, n+2, . . . , n+m on a second subject are performed. Moreover, even in the case of the second subject being a different person, the distances between the trials 1, 2, . . . , n do not change. Thus, as described later, it may be possible to calculate part of the distance matrix S that is calculable as just stated at the time of user registration and calculate the remaining elements at the time of authentication. Additionally, the distance matrix S is generally a symmetric matrix.

Therefore, using the symmetricity, it may be possible to calculate, for example, only the elements in the upper triangular part and obtain the remaining part from the calculated upper triangular part. With such an artifice, it is possible to eliminate duplicated calculation and expedite the processing.

Then, the determiner 105 obtains the possibility that the trials 1, 2, . . . , n and the trials n+1, n+2, . . . , n+m are classified into two different clusters from the calculated distance matrix S and determines whether the first subject and the second subject are different individuals or the same individual based on the possibility. The possibility obtained here expresses an indicator or a degree such as a reasonability, a sureness, a certainty, a likelihood, or a probability that the trials 1, 2, . . . , n and the trials n+1, n+2, . . . , n+m are classified into two different clusters. In other words, the possibility obtained here is low when the trials 1, 2, . . . , n, n+1, n+2, . . . , n+m are not classified into two clusters or, if classified, the trials 1, 2, . . . , n and the trials n+1, n+2, . . . , n+m are not classified into different clusters from each other.

Here, generally and mostly, the determiner 105 outputs whether the first condition under which the trials 1, 2, ..., n are performed and the second condition under which the trials n+1, n+2, ..., n+m are performed are substantially different or not. If this difference results in classifying the trials under the first condition and the trials under the second condition into two different clusters, the distance between the two clusters (for example, the distance between the centers of the clusters, the distance between the nearest points of the cluster envelope curves, the average Mahalanobis' generalized distance of the distributions of the two clusters, or the like) can be used as an indicator indicating how different the first condition and the second condition are.

The possibility that a group 1 comprising the trials 1, 2, ..., n and a group 2 comprising the trials n+1, n+2, ..., n+m are classified into different clusters can be obtained by cluster analysis. Typical cluster analysis techniques include a technique using multidimensional scaling and a technique using hierarchical clustering.

The multidimensional scaling corresponds, for example, to drawing a two-dimensional map in which given that the distance between stereoscopic points different in altitude is known, the distance is reflected to some extent. In this embodiment, the trials 1, 2, ..., n, n+1, n+2, ..., n+m are placed into a low-dimensional space such as two-dimensional space by multidimensional scaling (MDS) based on the distance prescribed in the distance matrix S.

Then, the distribution of the group 1 is obtained from the positions where the trials 1, 2, ..., n are placed and the distribution of the group 2 is obtained from the positions where the trials n+1, n+2, ..., n+m are placed. Then, if the two sufficiently overlap with each other, it can be determined that the first subject and the second subject are the same individual.

Here, various kinds of tests can be used to determine whether the two sufficiently overlap with each other. For example, it is possible to determine the degree of the trials 1, 2, ..., n in the group 1 and the trials n+1, n+2, ..., n+m in the group 2 being classified into two different clusters using a support vector machine (SVM) and leave-one-out cross-validation (LOOCV). Details of this technique will be described later.

Additionally, the following test can be used. In other words, the average position and the positional variance of the trials are obtained from placement of all trials. Then, the probability distribution according to the separation distance between the average positions of the groups when all trials are divided into two groups is obtained from the obtained average position and variance of all trials.

On the other hand, the separation distance between the average position of the distribution of the group 1 and the average position of the distribution of the group 2 is calculated.

Then, the probability that the separation distance when all trials are divided into any two groups is equal to or larger than the separation distance between the average position of the distribution of the group 1 and the average position of the distribution of the group 2 is obtained from the above probability distribution. This probability is assumed to be the probability that the trials included in the group 1 and the trials included in the group 2 are not classified into two different clusters (all trials are classified into one cluster or the trials in the two groups are classified into multiple mixed clusters). Here, the possibility that the trials included in the group 1 and the trials included in the group 2 are classified into two different clusters corresponds to the value obtained by subtracting the above probability from 1.

If the probability is lower than 5% or lower than 1%, the null hypothesis that the group 1 and the group 2 are classified into the same cluster is rejected with the p value of 0.05 or the p value of 0.01. Therefore, it is possible to determine whether the first subject and the second subject are different individuals or the same individual from the possibility based on the probability.

On the other hand, in simplified description of hierarchical clustering, the trials 1, 2, ..., n, n+1, n+2, ..., n+m are classified into n+m groups of one each and then the groups close to each other in distance are repeatedly combined to create a dendrogram.

Here, the distances between the trials are defined by the distance matrix S. However, the distances between the groups are not defined by the distance matrix. Then, the following technique is used as the distances between the trials included in the two groups. In other words, the minimum distance is used in the simple connection method; the maximum distance, in the complete connection method; the average distance, in the group average method; and the median distance, in the median method.

Here, the Ward method is also widely used to create a dendrogram, in which hierarchical clustering is performed using combinations decreasing the variance of the distances within a group and increasing the variance outside the group.

After a dendrogram is created as described above, the possibility is obtained according to how the placement of the trials 1, 2, ..., n and the placement of the trials n+1, n+2, ..., n+m are distributed in the dendrogram.

For example, given that the larger one of the fraction occupied by the trials 1, 2, ..., n and the fraction occupied by the trials n+1, n+2, ..., n+m in each group is termed the occupancy in the group, the occupancy in each group is obtained when the number of groups reaches a specific number (for example, 2 to 4) in the dendrogram and the product of all of them is calculated. The product calculated here has a value from 0 to 1. The product is larger when the degree of each group being occupied by the trials from the same subject is higher while the product is smaller when the trials from different subjects are mixed.

Thus, the above product is assumed to be the possibility that the trials 1, 2, ..., n and the trials n+1, n+2, ..., n+m are classified into two different clusters. It is determined that the first subject and the second subject are different individuals if this possibility is higher than a specific value, and otherwise the same individual.

Additionally, a test may be performed by setting a null hypothesis similarly to the above multidimensional scaling, obtaining a probability according to the dendrogram based on the shape or the like of the dendrogram, and making comparison with the p value.

The control flow executed by the parts of the determination device 101 at the time of user registration and at the time of actual authentication will be described below. In the flowing explanation, for easier understanding, it is assumed that a single user (a first subject) is registered at the determination device 101 and there are one or more users (second subjects) to authenticate. When multiple users are registered, each user is given a user ID and the user ID is entered as appropriate so as to result in the case in which there is a single first subject.

(Processing at the Time of Registration)

Figure 3:
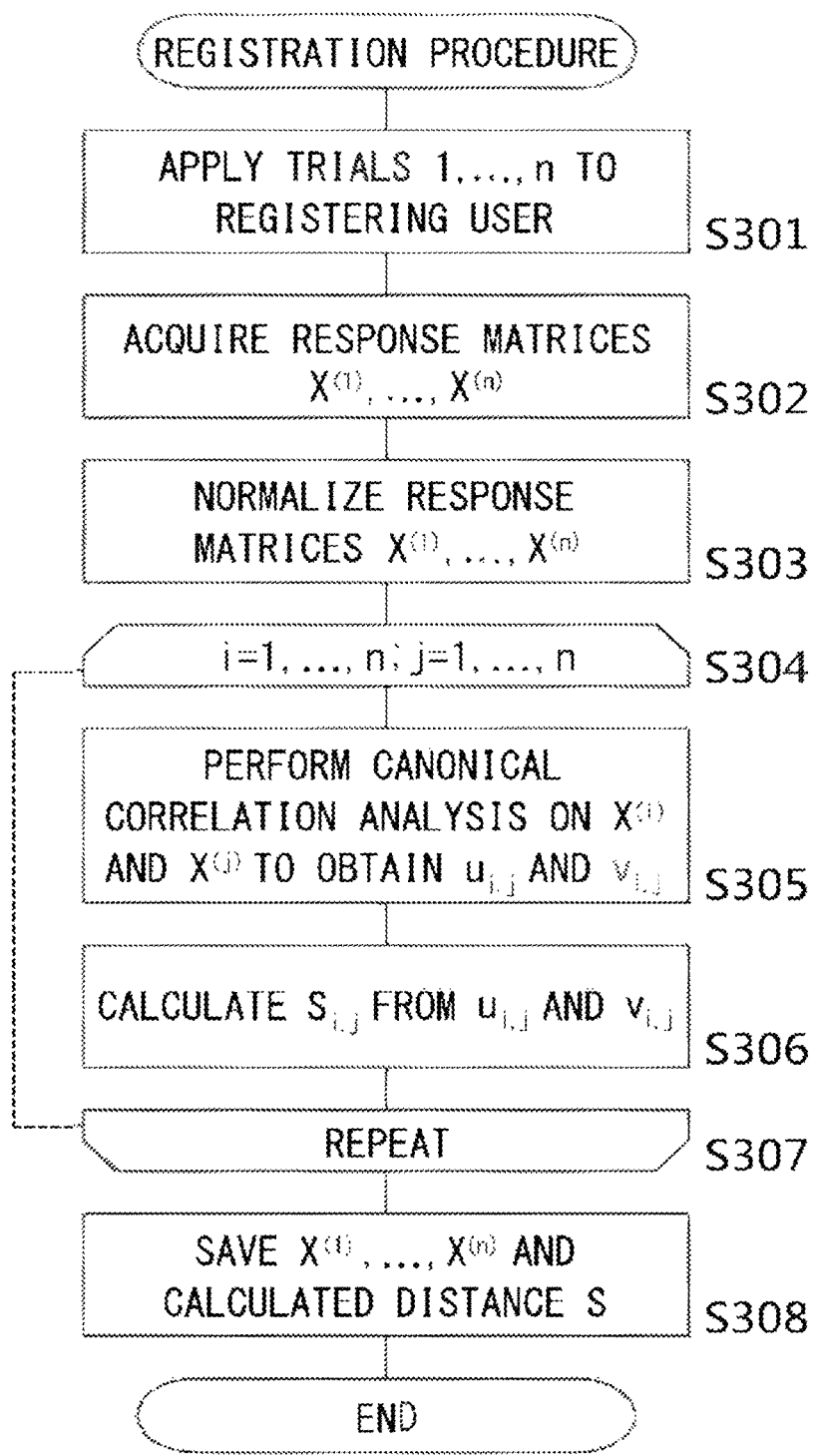
FIG. 3 is a flowchart showing the process flow of the registration procedure to register a first subject in the practical example of the present disclosure.

FIG. 3 is a flowchart showing the process flow of the registration procedure to register a first subject in the practical example of the present disclosure. The following explanation will be made with reference to this figure.

As the registration procedure starts, first, n trials (trial 1, trial 2, . . . , trial n) are applied to a registering user (a first subject) to register for measurement (Step S301). The trials may be performed by an operator in charge of registration or the registering user may wear an electroencephalograph on his own and start measuring.

Then, the acquirer 102 obtains response matrices $X^{(1)}, X^{(2)}, \ldots, X^{(n)}$ from the obtained measurements (Step S302).

Then, the analyzer 103 normalizes the response matrices $X^{(1)}, X^{(2)}, X^{(n)}$ to remove influence of noise and the like (Step S303).

Subsequently, the determination device 101 repeats the following processing for each of the integer i=1, 2, . . . , n and the integer j=1, 2, . . . , n (Step S304).

In other words, the analyzer 103 performs canonical correlation analysis on the response matrices $X^{(i)}$ and $X^{(j)}$ to obtain their respective first canonical time series $u_{i,j}$ and $v_{i,j}$ (Step S305).

Next, the distance calculator 104 calculates the elements $S_{i,j}$ of a distance matrix S from the first canonical time series $u_{i,j}$ and $v_{i,j}$ (Step S306).

After finishing the repetition (Step S307), the response matrices $X^{(1)}, X^{(2)}, \ldots, X^{(n)}$ normalized in the Step S303 and part of the distance matrix S calculated in the Step S306 are saved in a hard disk or the like in a nonvolatile manner in association with the registering user (the first subject) (Step S308) and the user registration ends.

(Processing at the Time of Authentication)

Figure 4:
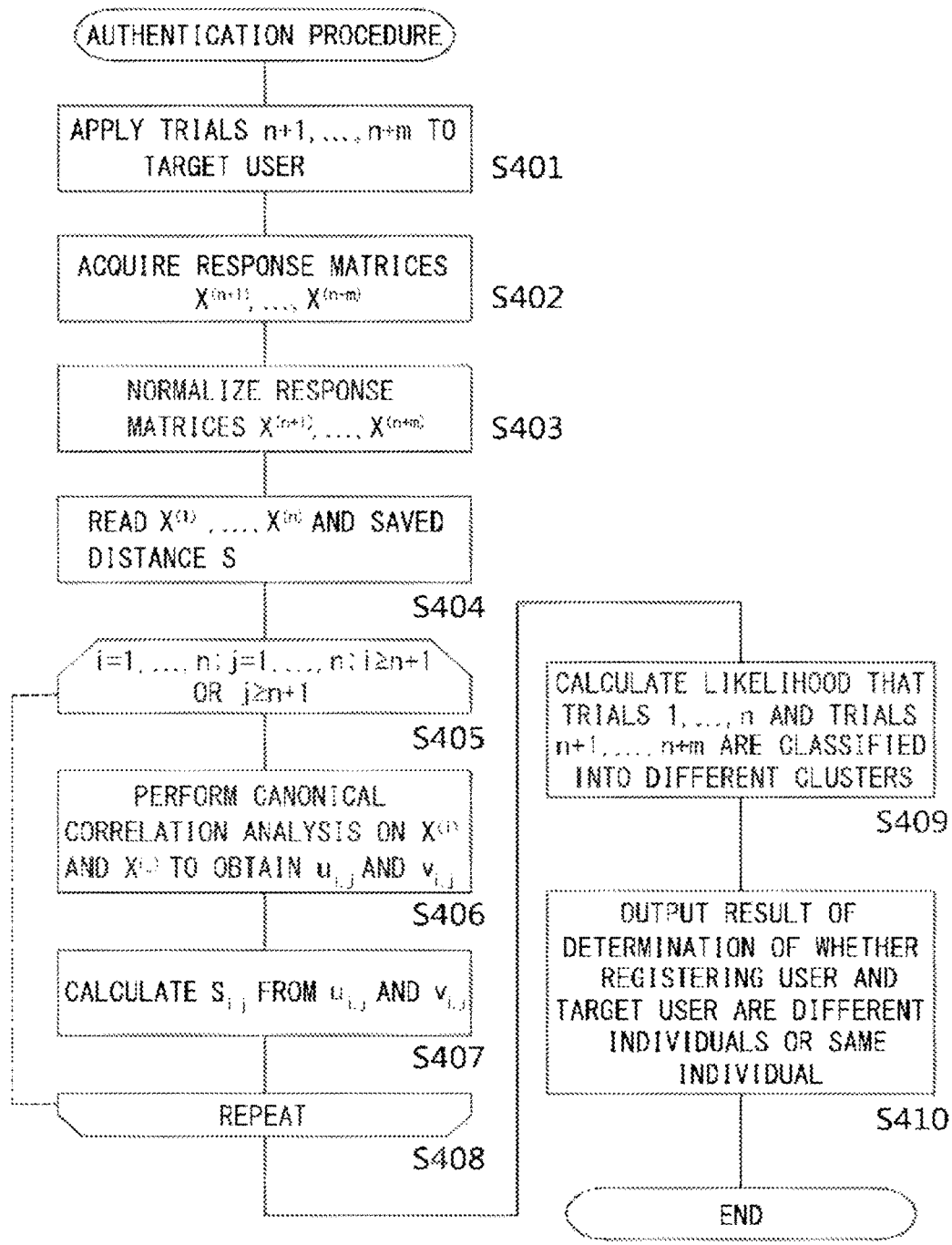
FIG. 4 is a flowchart showing the process flow of the authentication procedure to determine whether a second subject is different from or the same as the registered first subject in the practical example of the present disclosure.

FIG. 4 is a flowchart showing the process flow of the authentication procedure to determine whether a second subject is different from or the same as the registered first subject in the practical example of the present disclosure. The following explanation will be made with reference to this figure.

As the authentication procedure starts, first, m trials are applied to a target user (a second subject) for measurement (Step S401). As in the registration procedure, the trials may be performed by an operator in charge of registration or the target user may wear an electroencephalograph on his own and start measuring.

Then, the acquirer 102 obtains response matrices $X^{(n+1)}, X^{(n+2)}, \ldots, X^{(n+m)}$ from the obtained measurements (Step S402).

Then, the analyzer 103 normalizes the response matrices $X^{(n+1)}, X^{(n+2)}, \ldots, X^{(n+m)}$ to remove influence of noise and the like (Step S403).

Then, the determination device 101 reads onto the RAM or the like the response matrices $X^{(1)}, X^{(2)}, \ldots, X^{(n)}$ and the part of the distance matrix S saved in a nonvolatile manner for the registering user (Step S404).

Subsequently, the determination device 101 repeats the following processing for each of the cases satisfying i≥n+1 or j≥n+1 among the integer i=1, 2, . . . , n, n+1, n+2, . . . n+m and the integer j=1, 2, . . . , n, n+1, n+2, . . . , n+m (Step S405).

In other words, the analyzer 103 performs canonical correlation analysis on the response matrices $X^{(i)}$ and $X^{(j)}$ to obtain their respective first canonical time series $u_{i,j}$ and $v_{i,j}$ (Step S406).

Next, the distance calculator 104 calculates the elements $S_{i,j}$ of a distance matrix S from the first canonical time series $u_{i,j}$ and $v_{i,j}$ (Step S407).

After finishing the repetition (Step S408), the determiner 105 calculates the possibility that the group comprising the trials 1, 2, . . . , n and the group comprising the trials n+1, n+2, . . . n+m are classified into two different clusters based on the distance matrix S comprising the distances read in the Step S404 and the distances calculated in the Step S407 (Step S409).

Then, the determination result as to whether the registering user (the first subject) and the target (the second subject) are different individuals or the same individual is output based on the calculated possibility (Step S410). Here, generally and mostly, whether there is a substantial difference between a first condition under which n trials are performed and a second condition under which m trials are performed is output in the Step S410.

As the determination result, the possibility calculated in the Step S409 may be used as it is or it may be possible to determine whether the registering user (the first subject) and the target (the second subject) are different individuals or the same individual based on whether the possibility exceeds a threshold and output only this determined content.

As described above, this embodiment makes it possible to determine whether a first subject and a second subject are different individuals or the same individual using non-linear behavior of the human brain for authentication.

(Experimental Results)

Results of an experiment in which trials are performed based on the above-described design factors and processed by the determination device 101 to create a two-dimensional distribution of trials and a dendrogram will be described below.

Figure 5:
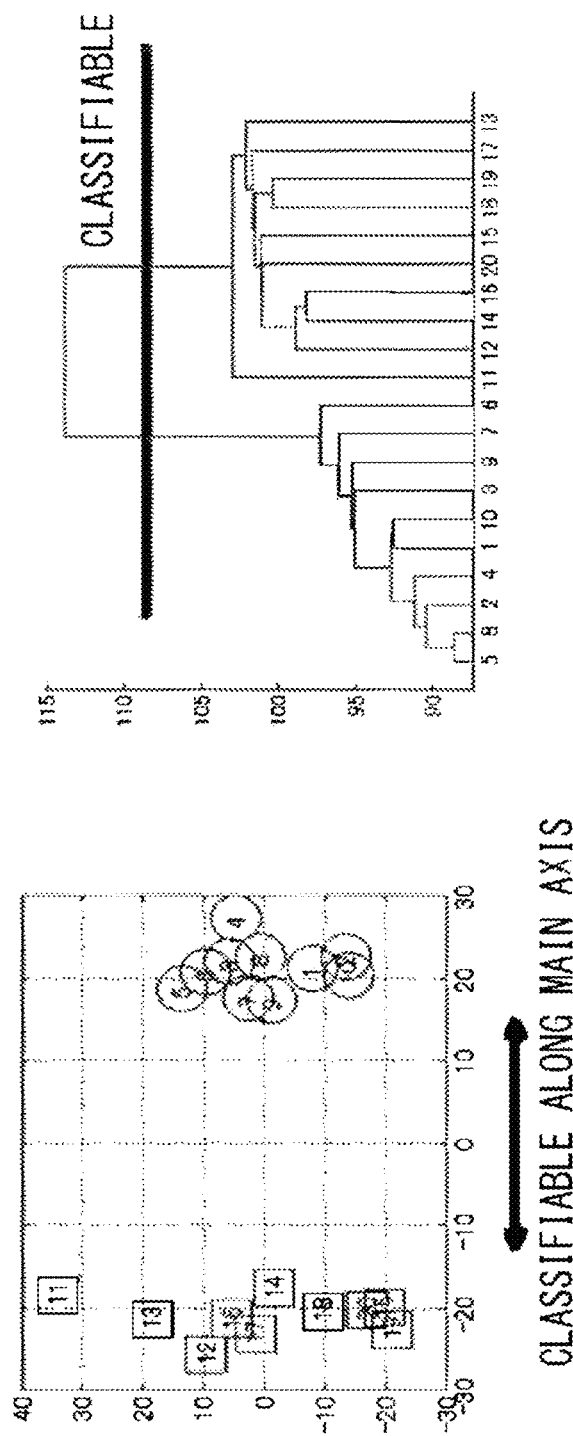
FIG. 5 is a two-dimensional distribution and a dendrogram created by performing trials with n=m=10 in which a first subject and a second subject are different individuals.
Figure 6:
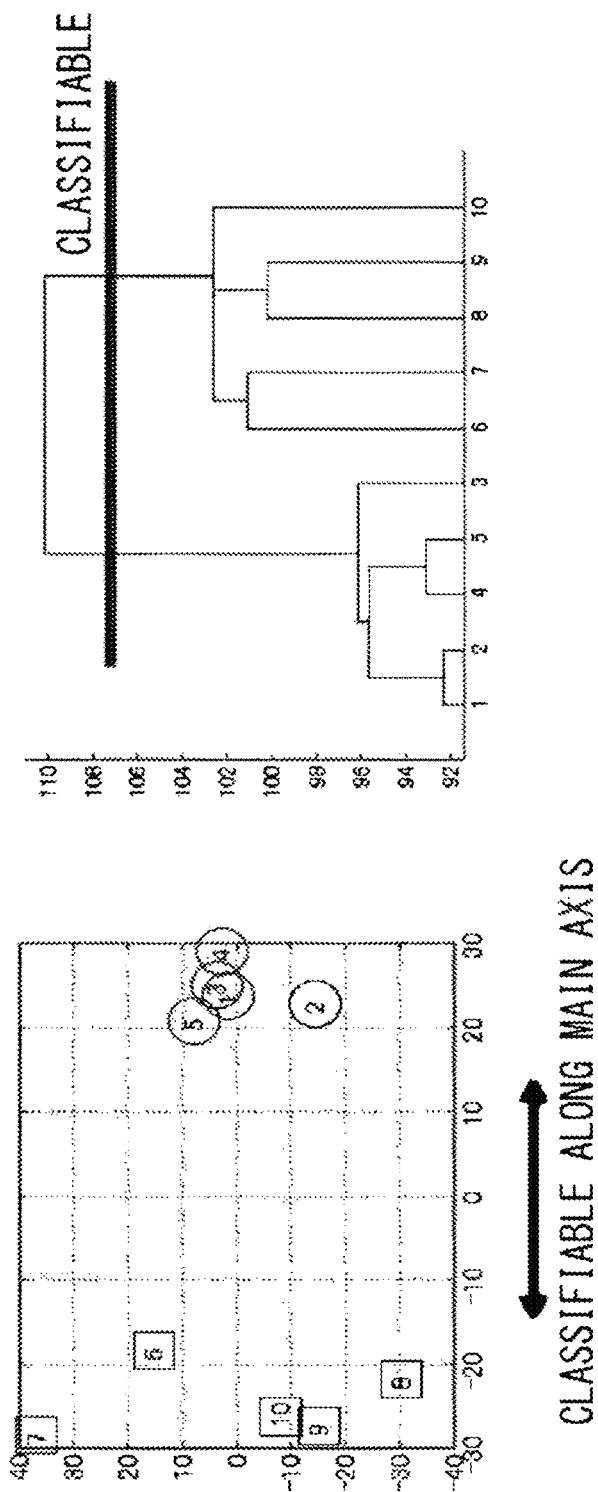
FIG. 6 is a two-dimensional distribution and a dendrogram created by performing trials with n=m=5 in which a first subject and a second subject are different individuals.

FIG. 5 is a two-dimensional distribution and a dendrogram created by performing trials with n=m=10 in which a first subject and a second subject are different individuals. Trials 1, 2, . . . , 10 were performed on the first subject and trials 11, 12, . . . , 20 are were performed on the second subject. FIG. 6 is a two-dimensional distribution and a dendrogram created by performing trials with n=m=5 in which a first subject and a second subject are different individuals. Trials 1, 2, . . . , 5 were performed on the first subject and trials 6, 7, . . . , 10 were performed on the second subject.

The charts on the left are the two-dimensional distributions of trials and the charts on the right are dendrograms.

As shown in the figures, it is seen that the two subjects were classified along the main axis of the multidimensional scaling. Moreover, it is seen that the two subjects were classified by the two upper clusters in the dendrograms.

Figure 7:
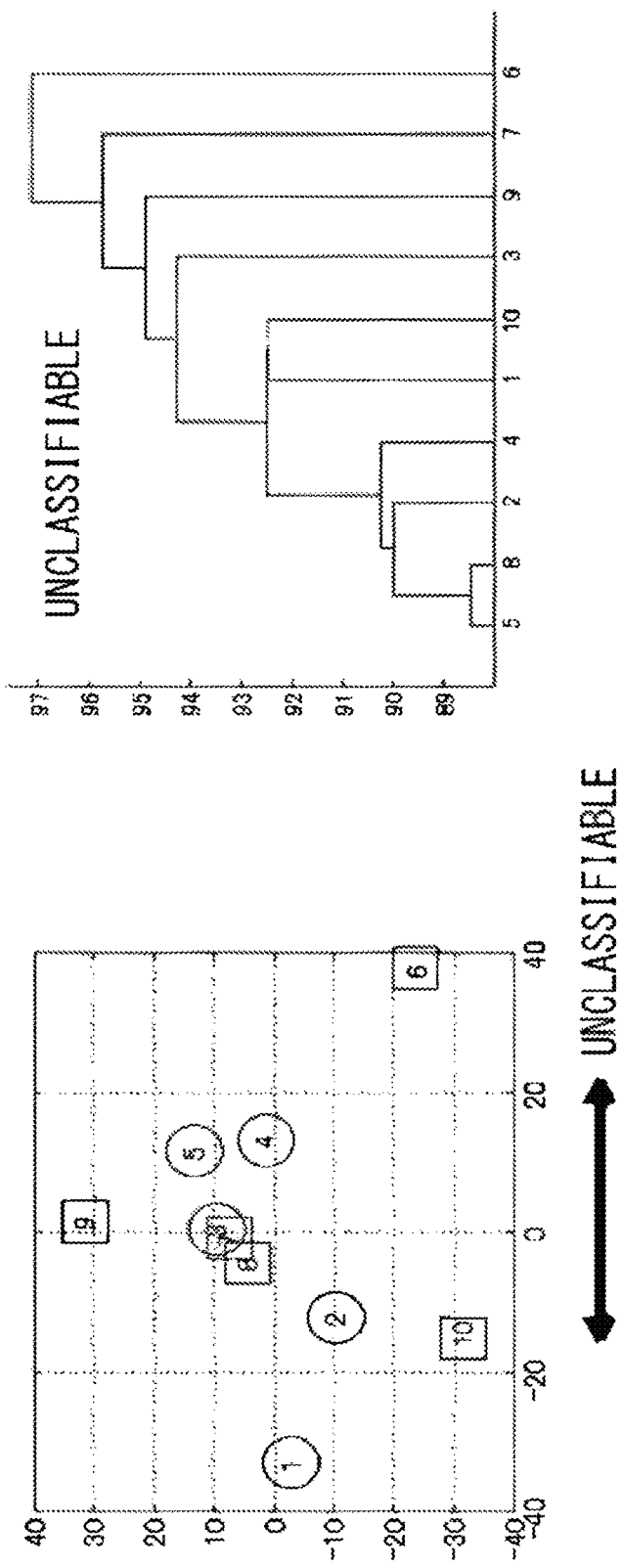
FIG. 7 is a two-dimensional distribution and a dendrogram created by performing trials with n=m=5 in which a first subject and a second subject are the same individual.

FIG. 7 is a two-dimensional distribution and a dendrogram created by performing trials with n=m=5 in which a first subject and a second subject are the same individual. Trials 1, 2, . . . , 5 and trials 6, 7, . . . , 10 were all performed on the first subject. As known from this figure, the two trials are placed in a mixture also in the multidimensional scaling. Moreover, the two are not classified but mixed also in the dendrogram.

(SVM and LOOCV)

Support Vector Machines (SVM) and Leave-One_Out Cross Validation (LOOCV) Support vector machines are widely used as a machine learning technique to find a boundary plane for classifying points belonging to either one of two clusters into the clusters. In this technique, any one trial is removed from trials 1, 2, . . . , n, n+1, n+2, . . . , n+m, and the remaining n+m−1 trials are applied to a support vector machine as teacher trials to obtain a boundary plane.

Then, leave-one-out cross-validation to determine whether the removed one trial is classified into the correct cluster by the boundary plane is used.

Here, one trial to remove is applied to all n+m trials and whether the trial is correctly classified is used as the possibility for determination.

If the trials are classified into two different clusters depending on the trial condition, the trials should be classified into correct clusters with a probability close to 100% no matter which trial is selected as the "leave-one-out" target.

On the other hand, if the trial conditions are substantially the same, the probability of being classified into correct clusters should be nearly 50%.

Figure 10:
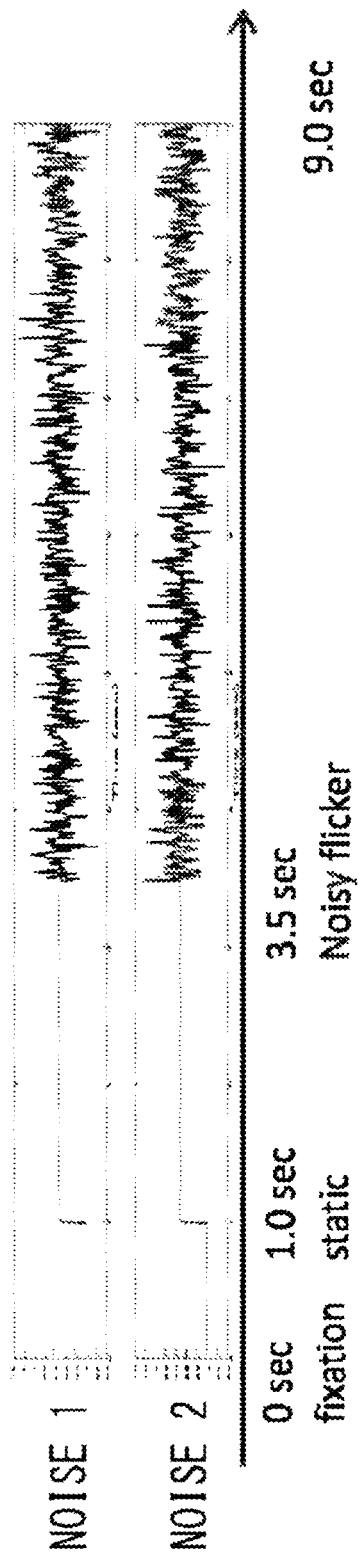
FIG. 10 is a graph showing the change with time of the contrast of the random video.

An experiment in the mode using the SVM/LOOCV will be described below. In the following experiment, first, 62 subjects were given 14 times a visual stimulus of viewing a random video (a total length of nine seconds) of two kinds of checkerboards (the number of squares is increased to 7×7) in which the contrast changed at 30 Hz in a white noise pattern of the Gaussian distribution, and the brain electrical activity was measured on 63 channels (for five seconds in the middle) to obtain response matrices. FIG. 10 is a graph showing the change with time of the contrast of the random video. Reaction of the subjects to the random video with noise 1 shown in this figure was analyzed.

Figure 8:
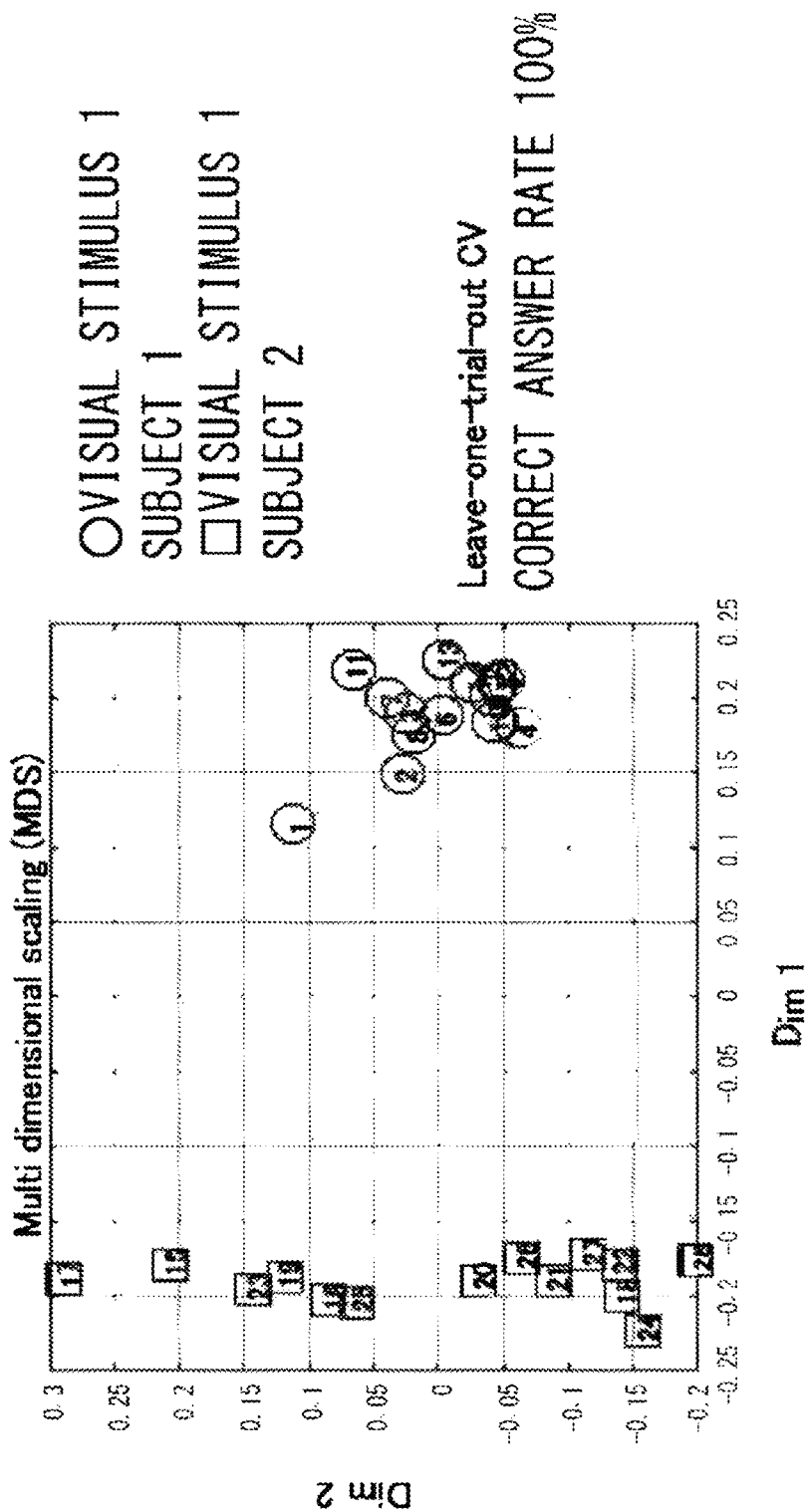
FIG. 8 is an explanatory chart presenting a lower dimensional distribution of trials in which the same content is provided to different subjects.

FIG. 8 is an explanatory chart presenting a lower dimensional distribution of trials in which the same content is provided to different subjects. This figure shows the distributions of trials on two subjects. A subject 1 is presented by light gray circles and a subject 2 is presented by dark gray squares. Although it is obvious from the figure that the two subjects are distinguished, the correct answer rate by the SVM/LOOCV is 100% and therefore it can be said that the two are classified into two different clusters.

The number of pairs selected from 62 subjects is $_{\{62\}}C_2$=1891. Each pair was examined as to whether the trials were classified into two different clusters on the subject basis by the SVM/LOOCV, and 98.29% were correct determination results.

When the same determination was performed by measuring the subjects while they were in a resting state, the correct answer rate was 88.30%. Thus, it is understood that this technique significantly improves the capability of distinguishing users.

When the same experiment was performed using only 19 channels instead of using all 63 channels of the measuring results, the correct answer rate by this technique was 93.74% and the correct answer rate in the resting state was of 62.6%. Thus, it is understood that this technique can distinguish users with considerably high performance even when the number of channels is reduced for saving the measuring cost and/or labor.

Furthermore, the same experiment was performed on the 62 subjects again one month later and the effectiveness of this technique over time as to whether the same subject can be determined to be the same one was examined.

Figure 9:
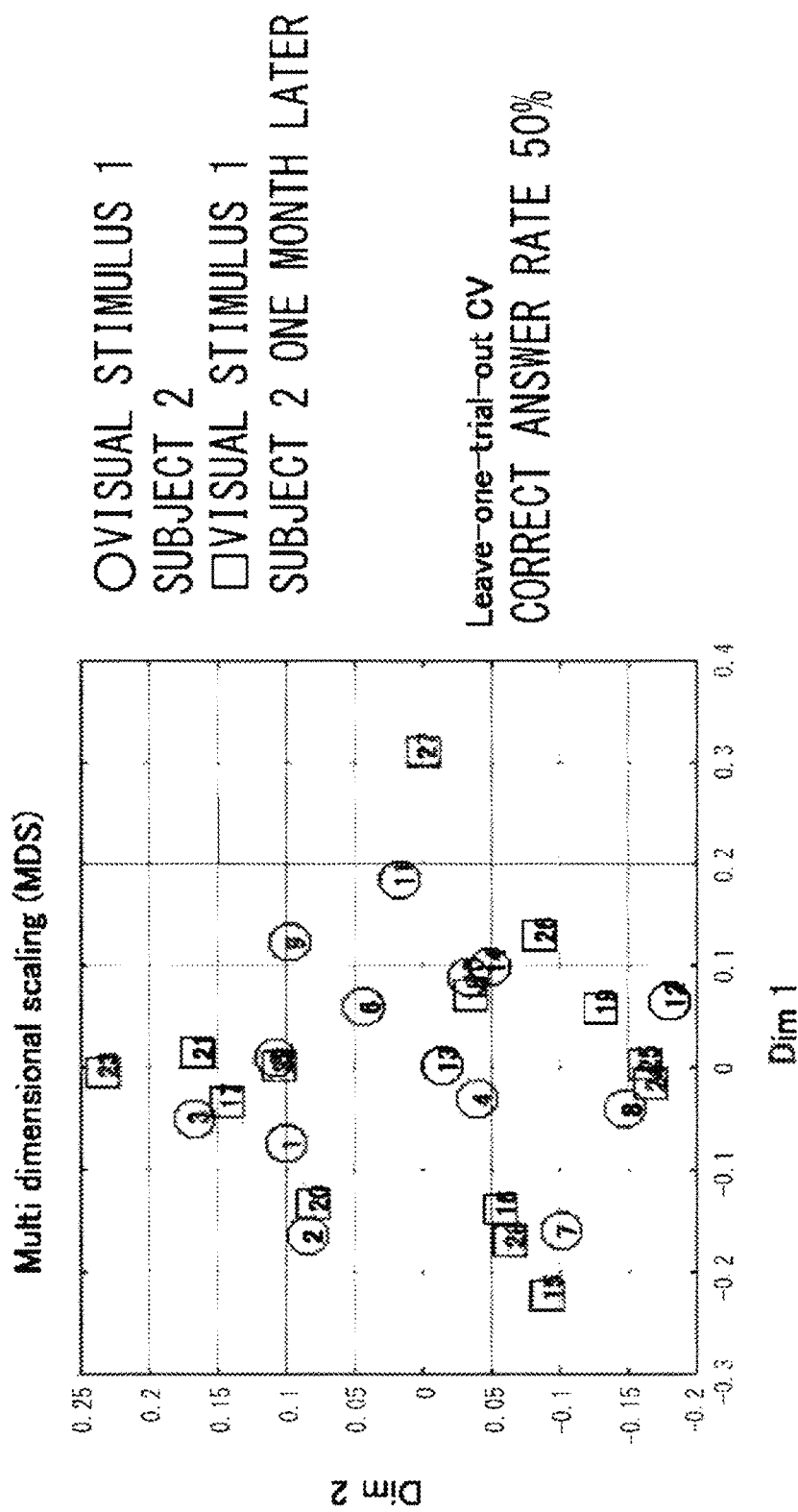
FIG. 9 is an explanatory chart presenting a lower dimensional distribution of trials in which the same content is provided to the same subject at a one-month interval.

FIG. 9 is an explanatory chart presenting a lower dimensional distribution of trials in which the same content is provided to the same subject at a one-month interval. This figure shows the trials on a subject in the first experiment by light grey circles and squares, and the trials one month later by dark gray circles and squares. As the SVM/LOOCV was executed on those, the correct answer rate was 50%. This is the same correct answer rate as when clusters are randomly selected and the two sufficiently overlap with each other. Therefore, it is understood that the first time and one month later are not classified into two clusters.

Such an experiment was performed on 23 subjects. The SVM correct answer rate resulting in classification into two different clusters at the first time and one to three months later was 74.53% with the use of 63 channels. This is significantly lower than the SVM correct answer rate of 98.29% when 62 different individuals were classified. Thus, it is possible to determine whether it is the same person using as an indicator the SVM correct answer rate or the distance between clusters in the MDS space.

Here, in the above-described experiments, measuring was performed with two kinds of random videos having noise 1 and noise 2. Therefore, it is possible to attempt the determination on the premise that the target person is the same individual in all trials 1, 2, . . . , n, n+1, n+2, . . . , n+m and observes a first random video in the trials 1, 2, . . . , n and a second random video in the trials n+1, n+2, . . . , n+m, and other conditions are the same as in the above-described experiments.

The first random video and the second random video are random videos in which the contrast of a checkerboard changes randomly and different in random number sequence. Noise 1 and noise 2 shown in FIG. 10 correspond contrast change of the first random video and the second random video, respectively.

Figure 11:
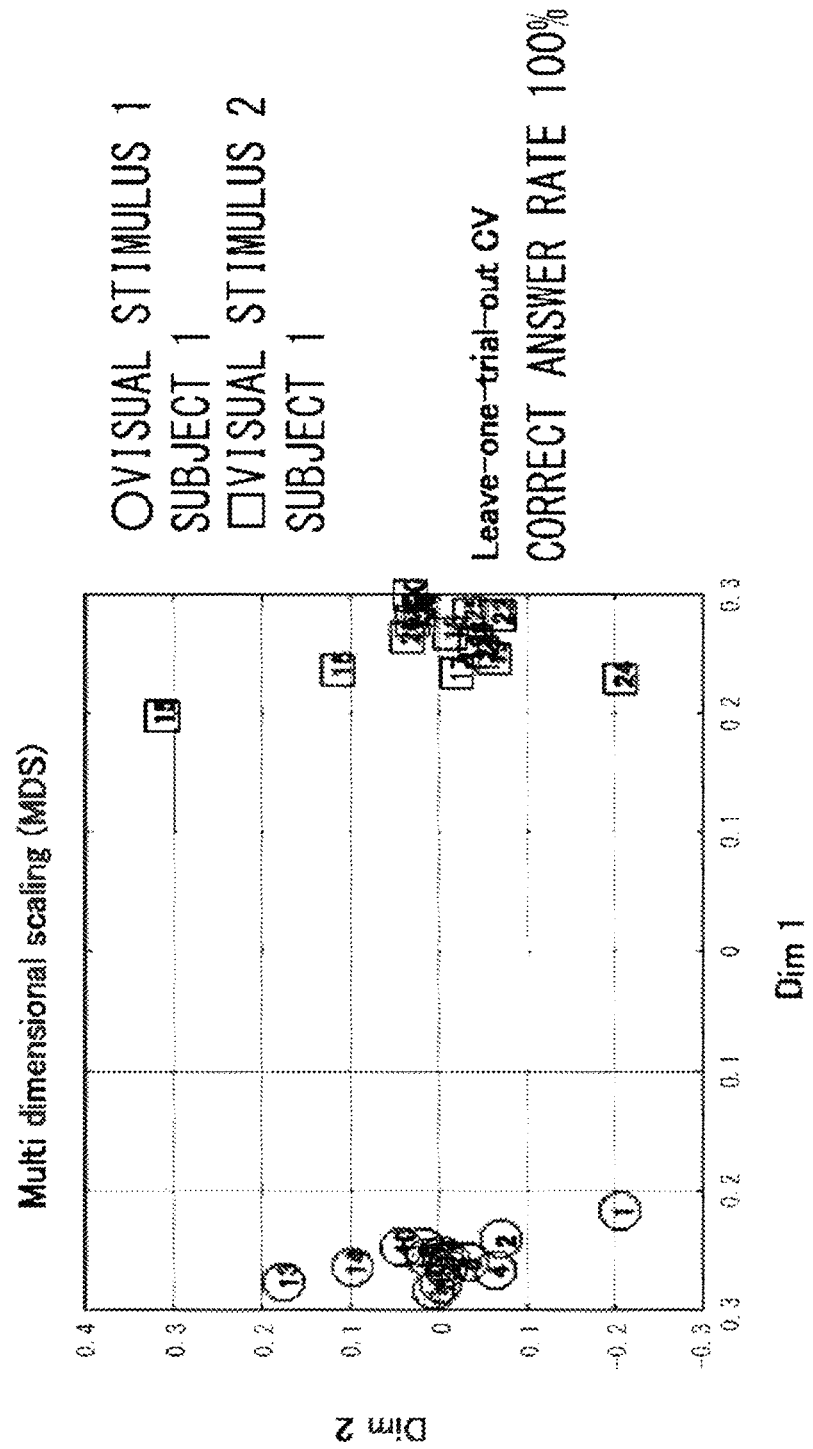
FIG. 11 is an explanatory chart presenting a lower-dimensional distribution of trials in which different contents are provided to the same subject.

FIG. 11 is an explanatory chart presenting a lower dimensional distribution of trials in which different contents are provided to the same subject. This figure shows the distribution of trials on a subject, in which the trials with the first random video (visual stimulus 1) are presented by light gray circles and the trials with the second random video (visual stimulus 2) are presented by dark gray squares.

As shown in this figure, it is seen that when different visual stimuli are given to a target person, the trials 1, 2, . . . , n and the trials n+1, n+2, . . . , n+m are classified into two different clusters even though the target person is the same individual.

Therefore, the principle of the present disclosure is obviously applicable to determining whether the target person is different/the same and further applicable to determining difference in brain reaction, interest, or preference of a single target person with respect to contents provided to the single target person. Moreover, an embodiment for authentication is applicable to determining interest or preference as it is simply by setting trial conditions such as providing the same target person with a first content under a first condition and a second content under a second condition.

When a single target person has the same degree of interest in two contents and the single target person does not distinguish the two contents, the trials 1, 2, . . . , n, n+1, n+2, . . . , n+m are not classified into two different clusters by content. They are classified into one cluster or classified into multiple clusters in which the two trials are mixed.

Generally, if trials 1, 2, . . . , n in which a content presenting a reference thing serving as the criterion of interest is provided (a first condition) and trials n+1, n+2, . . . , n+m in which a content presenting a thing for survey to know the degree of interest of the target person is provided (a second condition) are performed on a target person and the trials under the first condition and the trials under the second condition are classified into two different clusters, it is understood that the target person distinguishes the reference thing and the survey thing.

Moreover, as the cluster distribution is narrower, it is expected that the degree of interest in the thing is higher. Therefore, by comparing the size of the cluster for a reference thing and the size of the cluster for a survey thing, it is possible to determine the magnitude of interest or preference of the target person with respect to the two things.

Such determination of the interest or the preference will be described in detail in an exemplary application described later including types of the content to be provided.

(Calculation of the Distance Matrix)

As described below, various kinds of processing can be applied to the first canonical variable time series $u_{i,j}$ and $v_{i,j}$ in calculation of the distance matrix.

In the first technique, the distance calculator 104 applies a frequency filter to the first canonical variable time series $u_{i,j}$ and $v_{i,j}$, and performs the Hilbert transform to obtain imaginary parts and generate analytical signals so as to obtain instantaneous phase time series $\Phi$ [$u_{i,j}$] and $\Phi$ [$v_{i,j}$].

Then, the distance calculator 105 calculates the elements $S_{i,j}$ by the sum of absolute values of differences, the average of absolute values of differences, the square sum of differences, or the square average of differences of the instantaneous phase time series $\Phi$ [$u_{i,j}$] and $\Phi$ [$v_{i,j}$] or other distance calculation techniques.

In the second technique, the distance calculator 104 applies a frequency filter to the first canonical variable time series $u_{i,j}$ and $v_{i,j}$ and performs a wavelet transform to obtain instantaneous phase time series $\Phi$ [$u_{i,j}$] and $\Phi$ [$v_{i,j}$].

Then, the distance calculator 105 calculates the elements $S_{i,j}$ by the sum of absolute values of differences, the average of absolute values of differences, the square sum of differences, or the square average of differences of the instantaneous phase time series $\Phi$ [$u_{i,j}$] and $\Phi$ [$v_{i,j}$] or other distance calculation techniques.

The frequency filter used here may be the same one as applied to the response matrices or a different one.

As described above, this practical example makes it clear that various modes can be used as the distance calculation technique. The distance calculation technique can be switched as appropriate according, for example, to the type of the random video, the type and capability of the electroencephalograph, and the like.

(Types of the Content)

In the above explanation, the content for the target person to observe is exemplified by a random video such as a checkerboard video in which the contrast changes randomly, a white noise video, and a pink noise video. Other videos and various kinds of sound information can be used as the content.

Figure 12:
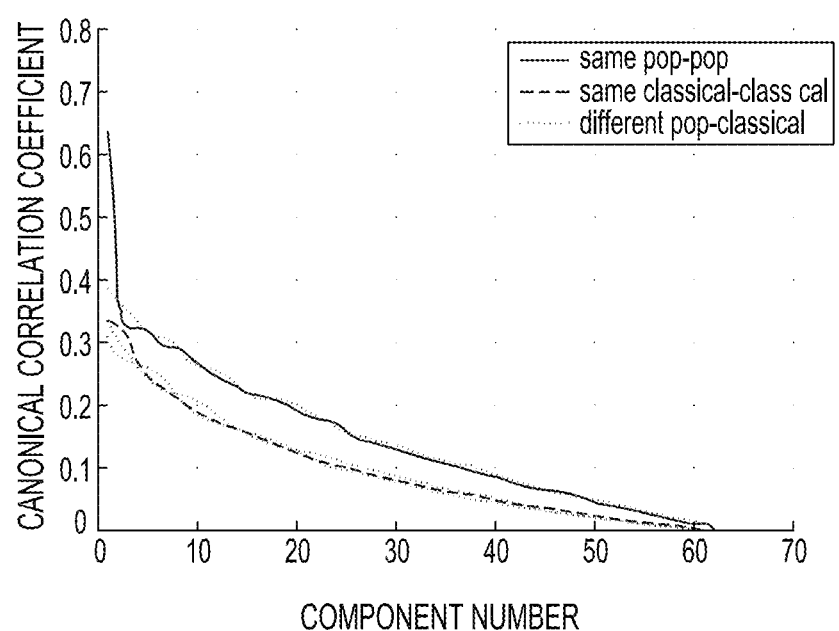
FIG. 12 is a graph showing the tendency of canonical correlation coefficients obtained by performing canonical correlation analysis on response matrices obtained in trials in which the subject listens to one kind of pop music and one kind of classical music two times each.

For example, a case of using sound signals of various kinds of music as the contents is discussed. Then, an experiment was conducted in which a total of two pieces of music, pop music (pop) and classical music with a monotonous rhythm (classical), were used as the content and each trial under a first condition or a second condition that either of the two was used as the content was performed two times. Then, canonical correlation analysis was performed and the values of the canonical correlation coefficients were compared in the order of strong components (in the order of component numbers). FIG. 12 is a graph showing the tendency of canonical correlation coefficients obtained by performing canonical correlation analysis on the response matrices obtained in the trials in which the target person listened to one kind of pop music and one kind of classical music two times each. As shown in this figure, the correlation between pop music and pop music with a good beat (same pop-pop) is higher than the correlation between classical music and classical music with a monotonous rhythm (same classical-classical) and also higher than the correlation between pop music and classical music (different pop-classical).

In this experiment, the target person was in the generation favoring pop music. Therefore, presumably, with the content the target person is interested in, the correlation between trials is high, the distance between trials is small, and the clusters have a small variance even in a lower dimensional space.

Figure 13:
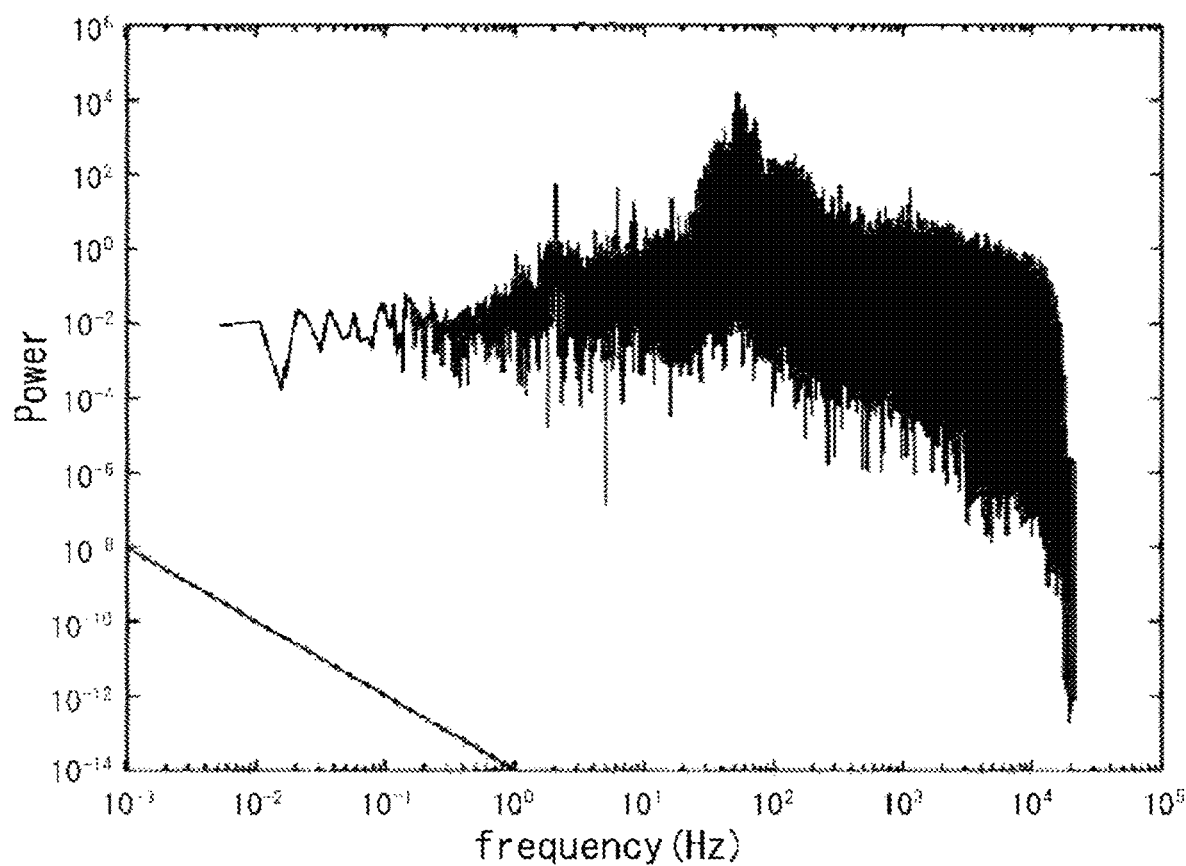
FIG. 13 is the power spectrum of a piece of pop music.
Figure 14:
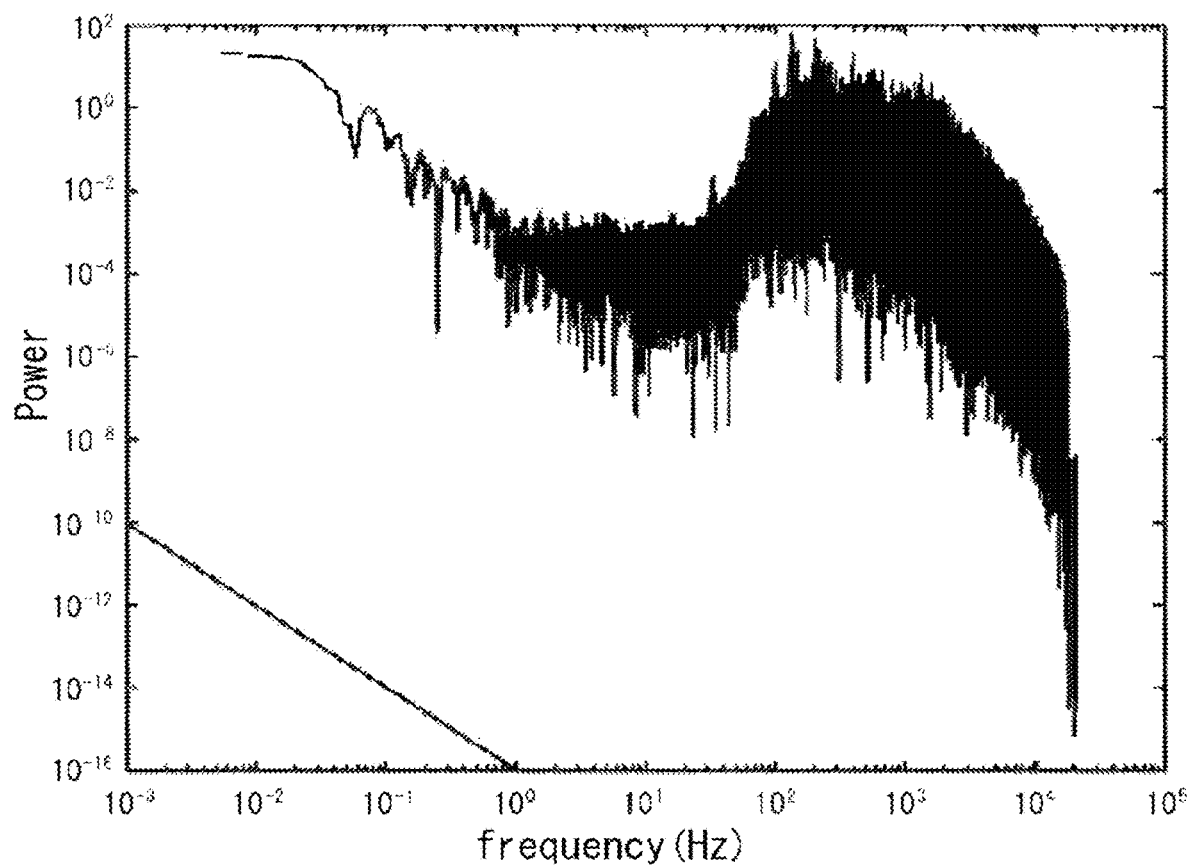
FIG. 14 is the power spectrum of a piece of classical music.

Furthermore, the power spectra in the spatiotemporal direction of both categories of music are compared. FIG. 13 is the power spectrum of a piece of pop music. FIG. 14 is the power spectrum of a piece of classical music. In those figures, in addition to the power spectrum of the music piece, the inclination (−2) of the power spectrum of Brownian noise is drawn in the bottom left corner of the graph.

It is known from the graphs that both pieces of music evenly include many frequency components from low frequencies to high frequencies. Moreover, a random video changing according to white noise, pink noise, Brownian noise, or gray noise also evenly include frequency components.

Therefore, presumably, it is desirable for performing various kinds of distinction that the content to provide to the target person evenly include many frequency components from low frequencies to high frequencies.

A possible technique of determining whether a content is suitable is as follows. First, a power spectrum of any of white noise, pink noise, Brownian noise, and gray noise is set as a reference spectrum. Then, the similarity between the power spectrum of a content and the reference spectrum is calculated using, for example, the correlation coefficients of the form of the spectrum envelope, or the distance or the angle between the vectors constituted by the power spectra of a dimension equal in number to frequency steps. Then, if the similarity is lower than a given threshold, it is determined that it is not a suitable content for this embodiment.

A video or recorded sound of nature and recorded sound of a living body or musical performance of a non-electronic acoustic musical instrument evenly include a wide range of frequency components and highly similar to the reference spectrum.

Therefore, a content using the above can be considered to be a suitable content for providing to the user in this technique.

Additionally, a video displaying multiple pictures in a short time (for example, one- to three-frame time length of a 60 FPS video) randomly and successively can be used as a random video.

Furthermore, using, as a content to provide, display of
pictures of items belonging to a specific category, or
pictures in which human facial expression expressing specific emotion (anger, fear, joy, sadness, and the like) is captured with the brightness contrast switched in a very short time like noise, multiple trials are performed in which this random video is shown to the same target person (the first subject). Then, obtaining the distance matrix as in the above practical example, it is possible to examine the reaction of the target person (the first subject) to the category, namely the degree of interest.

In other words, it is possible to calculate the average or the variance of elements included in a distance matrix or the extension or the variance in the main axis direction or the extension or the variance in the sub-axis direction of the placement of the distance matrix reduced in dimension by multidimensional scaling, and consider that the target person (the first subject) has consistent reaction to the items and is interested in them as the obtained value is lower.

Then, the consistency calculated as described above can be used as a measure of the degree of preference, interest, or emotional reaction of the target person (the first subject) with respect to the items.

Moreover, it is possible to obtain the tendency of preference or emotional reaction of a group to a category by making multiple subjects belonging to a certain group observe the items video multiple times, calculating the degree of preference or emotional reaction, and obtaining the distribution (the average, the variance, or the like).

As described above, when the target person is the same subject and the content to provide is different under the first condition and the second condition, it is possible to determine the difference in interest or preference of the target person to the contents or things indicated by the contents.

For example, the same subject observes a first object or a second object along with a random image and then it is determined whether the trials in which the first object is shown and the trials in which the second object is shown are classified into two different clusters by applying the canonical correlation analysis, the reduction in dimension, and the SVM/LOOCV as described above. If they are classified into two different clusters sufficiently apart from each other, it is known that there is a sufficient difference in interest between the first object and the second object.

If there is a difference, the degrees of interest in the first object and the second object are obtained from the distributions of the clusters, in other words the densities of the clusters or the smallness of the clusters. The degree of interest in the object is considered to be high as the density of the cluster is higher or the size of the cluster is smaller.

As a technique of making an object observed along with a random image, for example, it is possible to combine, as an inset or as a translucent image, an image of a first object and an image of a second object in a part, for example at the center, of a random image of a checkerboard in the trials 1, 2, . . . , n and in the trials n+1, n+2, . . . , n+m, respectively. Moreover, it may also be possible to combine as a translucent image a first object image or a second object image on the entire checkerboard.

Furthermore, as another technique, it is also possible to insert a first object image or a second object image at a position of a specific frame number (one or multiple) in a random video.

According to the above-described criterion for determining whether a content is suitable, a still image is not a suitable content to provide. Then, as described above, if a random video and still images of a first object and a second object are provided in a composite form, a content suitable for this technique is obtained and the difference in interest or the degree of interest in the objects can be calculated.

SUMMARY

As described above, the determination device according to the present disclosure comprises:

an acquirer acquiring (n+m) response matrices by measuring brain electrical activity of a target person in n trials under a first condition and m trials under a second condition;

an analyzer performing canonical correlation analysis on response matrices included in the acquired (n+m) response matrices to obtain first canonical variable time series for the response matrices;

a distance calculator calculating a distance between the trials for the response matrices from the obtained first canonical variable time series; and a determiner obtaining a possibility that the n trials and the m trials are classified into two different clusters from the calculated distance and determining whether the first condition and the second condition are substantially different based on the possibility.

The determination device can be configured as follows:
in the n trials, a first subject is the target person and observes a predetermined content, in the m trials, a second subject is the target person and observes the predetermined content, and whether the first subject and the second subject are different individuals or the same individual is determined based on the obtained possibility.

The determination device can be configured as follows:
the predetermined content has a power spectrum of which a similarity to white noise, pink noise, Brownian noise, or gray noise is equal to or higher than a given threshold.

The determination device can be configured as follows:
the predetermined content is a random video, a video or recoded sound of nature, recorded sound of a living body or musical performance of an acoustic musical instrument, or a content using these.

The determination device can be configured as follows:
a first content is provided to the target person under the first condition, a second content is provided to the target person under the second condition, and whether there is a difference in interest of the target person between the first content and the second content is determined based on the obtained possibility.

The determination device can be configured as follows:
the first content and the second content have a power spectrum of which a similarity to white noise, pink noise, Brownian noise, or gray noise is equal to or higher than a given threshold.

The determination device can be configured as follows:
the first content and the second content are a random video, a video or recoded sound of nature, recorded sound of a living body or musical performance of an acoustic musical instrument, or contents using these and different from each other.

The determination device can be configured as follows:
the target person observes a predetermined random video and a first object under the first condition, the target person observes the predetermined random video and a second object under the second condition, and whether there is a difference in interest of the target person between the first object and the second object is determined based on the obtained possibility.

The determination device can be configured as follows:
the determiner obtains a first degree of interest of the target person under the first condition from a distribution of a first cluster into which the n trials are classified and obtains a second degree of interest of the target person under the second condition from a distribution of a second cluster into which the m trials are classified.

The determination device can be configured as follows:
brain electrical activity at D points of a target person is measured T times in the n trials 1, 2, . . . , n and in the m trials n+1, n+2, . . . , n+m, for each of an integer i (i=1, 2, . . . , n, n+1, n+2, . . . , n+m), an integer p (p=1, 2, . . . , D), and an integer t (t=1, 2, . . . , T), an element $X^{(i)}_p(t)$ in a row p and a column t of a response matrix $X^{(i)}$ obtained in the trial i is a value measured at a p-th point among the D points at a t-th sampling time since the random video observation starts, for each of the integer i (i=1, 2, ..., n, n+1, n+2, ..., n+m) and an integer j (j=1, 2, ..., n, n+1, n+2, ..., n+m), canonical correlation analysis is performed on the response matrix $X^{(i)}$ for the trial i and the response matrix $X^{(j)}$ for the trial j to obtain a first canonical variable time series $u_{i,j}$ for the response matrix $X^{(i)}$ and a first canonical variable time series $v_{i,j}$ for the response matrix $X^{(j)}$, and for each of the integer i (i=1, 2, ..., n, n+1, n+2, ..., n+m) and the integer j (j=1, 2, ..., n, n+1, n+2, ..., n+m), an element $S_{i,j}$ in a row i and a column j of a distance matrix S is assumed to be a distance between the trial i and the trial j that is calculated from the first canonical variable time series $u_{i,j}$ and the first canonical variable time series $v_{i,j}$.

The determination device can be configured as follows: the determiner obtains the possibility from the distance matrix S by placing the trials 1, 2, ..., n, n+1, n+2, ..., n+m in a low-dimensional space by multidimensional scaling and applying a support vector machine and leave-one-out cross-validation to the trials 1, 2, ..., n, n+1, n+2, ..., n+m placed in the low-dimensional space.

The determination device can be configured as follows: the determiner places the trials 1, 2, ..., n, n+1, n+2, ..., n+m in a low-dimensional space from the distance matrix S by multidimensional scaling and obtains the possibility from overlap between a distribution of the n trials and a distribution of the m trials in the low-dimensional space.

The determination device can be configured as follows: the determiner creates from the distance matrix S a dendrogram in which the trials 1, 2, ..., n, n+1, n+2, ..., n+m are clustered by hierarchical clustering and obtains the possibility from placement of the n trials and placement of the m trials in the dendrogram.

The determination device can be configured as follows: the distance calculator calculates the elements $S_{i,j}$ by the sum of absolute values of differences, the average of absolute values of differences, the square sum of differences, or the square average of differences of the first canonical variable time series $u_{i,j}$ and the first canonical variable time series $v_{i,j}$.

The determination device can be configured as follows: the distance calculator applies a frequency filter to the first canonical variable time series $u_{i,j}$ and $v_{i,j}$, performs the Hilbert transform to obtain imaginary parts and generate analytical signals so as to obtain instantaneous phase time series $\Phi[u_{i,j}]$ and $\Phi[v_{i,j}]$, and calculates the elements $S_{i,j}$ by the sum of absolute values of differences, the average of absolute values of differences, the square sum of differences, or the square average of differences of the instantaneous phase time series $\Phi[u_{i,j}]$ and $\Phi[v_{i,j}]$.

The determination device can be configured as follows: the distance calculator applies a frequency filter to the first canonical variable time series $u_{i,j}$ and $v_{i,j}$, performs a wavelet transform to obtain instantaneous phase time series $\Phi[u_{i,j}]$ and $\Phi[v_{i,j}]$, and calculates the elements $S_{i,j}$ by the sum of absolute values of differences, the average of absolute values of differences, the square sum of differences, or the square average of differences of the instantaneous phase time series $\Phi[u_{i,j}]$ and $\Phi[v_{i,j}]$.

The determination device can be configured as follows: the analyzer performs canonical correlation analysis after normalizing amplitudes of the response matrices $X^{(1)}, X^{(2)}, \ldots, X^{(n)}, X^{(n+1)}, X^{(n+2)}, \ldots, X^{(n+m)}$ or applying a frequency filter to the response matrices $X^{(1)}, X^{(2)}, \ldots, X^{(n)}, X^{(n+1)}, X^{(n+2)}, \ldots, X^{(n+m)}$.

Moreover, in the determination method according to the present disclosure, a determination device acquires (n+m) response matrices by measuring brain electrical activity of a target person in n trials under a first condition and m trials under a second condition;

performs canonical correlation analysis on response matrices included in the acquired (n+m) response matrices to obtain first canonical variable time series for the response matrices;

calculates a distance between the trials for the response matrices from the obtained first canonical variable time series; and obtains a possibility that the n trials and the m trials are classified into two different clusters from the calculated distance and determines whether the first condition and the second condition are substantially different based on the possibility.

The program according to the present disclosure makes a computer function as parts possessed by the above-described determination device.

The non-transitory computer-readable information recording medium according to the present disclosure stores the above program.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

This application claims the priority based on Japanese Patent Application No. 2015-108664, filed in Japan on Thursday, May 28, 2015, and the content of this basic application is incorporated herein to the fullest legal extent in the designated nation.

INDUSTRIAL APPLICABILITY

The present disclosure can provide a determination device determining the presence/absence of substantial difference in trial condition such as the subject being different/the same or the presence/absence of difference in interest of the subject in an object by measuring the brain waves, a determination method, a program for realizing them by a computer, and a non-transitory computer-readable information recording medium storing the program.

REFERENCE SIGNS LIST

101 Determination device
102 Acquirer
103 Analyzer
104 Distance calculator
105 Determiner

What is claimed is:
1. A determination device, comprising:
an electroencephalograph that measures brain electrical activity of a target person with D electrodes in n trials under a first condition and m trials under a second condition;
an acquirer that acquires (n+m) response matrices from the measured brain electrical activity of the n and m trials;
an analyzer that performs canonical correlation analysis on response matrices included in the acquired (n+m)

response matrices to obtain first canonical variable time series for the response matrices;

a distance calculator that calculates a distance between the n and m trials for the response matrices from the obtained first canonical variable time series; and a determiner that obtains a possibility that the n trials and the m trials are classified into two different clusters from the calculated distance and determines whether the first condition and the second condition are different or not by comparing the possibility with a specific value, and wherein brain electrical activity at D points of a target person is measured, with the D electrodes respectively, T times in the n trials 1, 2, . . . , n and in the m trials n+1, n+2, n+m, for each of an integer i (i=1, 2, . . . , n, n+1, n+2, . . . , n+m), an integer p (p=1, 2, . . . , D), and an integer t (t=1, 2, . . . , T), an element $X^{(i)}_p(t)$ in a row p and a column t of a response matrix $X^{(i)}$ obtained in the trial i is a value measured at a p-th point among the D points at a t-th sampling time since the trial i starts, for each of the integer i (i=1, 2, . . . , n, n+1, n+2, . . . , n+m) and an integer j (j=1, 2, . . . , n, n+1, n+2, . . . , n+m), canonical correlation analysis is performed on the response matrix $X^{(i)}$ for the trial i and the response matrix $X^{(j)}$ for the trial j to obtain a first canonical variable time series $u_{i,j}$ for the response matrix $X^{(i)}$, and a first canonical variable time series $v_{i,j}$ for the response matrix $X^{(j)}$, and for each of the integer i (i=1, 2, . . . , n, n+1, n+2, . . . , n+m) and the integer j (j=1, 2, . . . , n, n+1, n+2, . . . , n+m), an element in a row i and a column j of a distance matrix S is assumed to be a distance between the trial i and the trial j that is calculated from the first canonical variable time series $u_{i,j}$ and the first canonical variable time series $v_{i,j}$, and wherein the determiner obtains the possibility from the distance matrix S by:

placing the n and m trials 1, 2, . . . , n, n+1, n+2, n+m in a low-dimensional space by multidimensional scaling and applying a support vector machine and leave-one-out cross-validation to the n and m trials 1, 2, . . . , n, n+1, n+2, n+m placed in the low-dimensional space;

placing the n and m trials 1, 2, . . . , n, n+1, n+2, . . . , n+m in a low-dimensional space from the distance matrix S by multidimensional scaling and measuring overlap between a distribution of the n trials and a distribution of the m trials in the low-dimensional space; or creating from the distance matrix S a dendrogram in which the n and m trials 1, 2, . . . , n, n+1, n+2, . . . , n+m are clustered by hierarchical clustering measuring placement of the n trials and placement of the m trials in the dendrogram.

2. The determination device according to claim 1, wherein in the n trials, a first subject is the target person and observes a predetermined content, in the m trials, a second subject is the target person and observes the predetermined content, and whether the first subject and the second subject are different individuals or the same individual is determined based on the obtained possibility.

3. The determination device according to claim 1, wherein a first content is provided to the target person under the first condition, a second content is provided to the target person under the second condition, and whether there is a difference in interest of the target person between the first content and the second content is determined based on the obtained possibility.

4. The determination device according to claim 3, wherein the determiner obtains a first degree of interest of the target person under the first condition from a distribution of a first cluster into which the n trials are classified and obtains a second degree of interest of the target person under the second condition from a distribution of a second cluster into which the m trials are classified.

5. The determination device according to claim 1, wherein the target person observes a predetermined random video and a first object under the first condition, the target person observes the predetermined random video and a second object under the second condition, and whether there is a difference in interest of the target person between the first object and the second object is determined based on the obtained possibility.

6. The determination device according to claim 5, wherein the determiner obtains a first degree of interest of the target person under the first condition from a distribution of a first cluster into which the n trials are classified and obtains a second degree of interest of the target person under the second condition from a distribution of a second cluster into which the m trials are classified.

7. The determination device according to claim 1, wherein the distance calculator calculates each element $S_{i,j}$ by the sum of absolute values of differences, the average of absolute values of differences, the square sum of differences, or the square average of differences of the first canonical variable time series $u_{i,j}$ and the first canonical variable time series $v_{i,j}$.

8. The determination device according to claim 1, wherein the distance calculator applies a frequency filter to the first canonical variable time series $u_{i,j}$ and $v_{i,j}$, performs Hilbert transform to obtain imaginary parts and generate analytical signals so as to obtain instantaneous phase time series $\Phi$ $[u_{i,j}]$ and $\Phi$ $[v_{i,j}]$, and calculates the elements $S_{i,j}$ by the sum of absolute values of differences, the average of absolute values of differences, the square sum of differences, or the square average of differences of the instantaneous phase time series $\Phi$ $[u_{i,j}]$ and $\Phi$ $[v_{i,j}]$.

9. The determination device according to claim 1, wherein the distance calculator applies a frequency filter to the first canonical variable time series $u_{i,j}$ and $v_{i,j}$, performs a wavelet transform to obtain instantaneous phase time series $\Phi$ $[u_{i,j}]$ and $\Phi$ $[v_{i,j}]$, and calculates each element $S_{i,j}$ by the sum of absolute values of differences, the average of absolute values of differences, the square sum of differences, or the square average of differences of the instantaneous phase time series $\Phi$ $[u_{i,j}]$ and $\Phi$ $[v_{i,j}]$.

10. The determination device according to claim 1, wherein the analyzer performs canonical correlation analysis after normalizing amplitudes of the response matrices $X^{(1)}, X^{(2)}, \ldots, X^{(n)}, X^{(n+1)}, X^{(n+2)}, \ldots, X^{(n+m)}$ or applying a frequency filter to the response matrices $X^{(1)}, X^{(2)}, \ldots, X^{(n)}, X^{(n+1)}, X^{(n+2)}, \ldots X^{(n+m)}$.

11. A determination method, wherein a determination device measures brain electrical activity of a target person with D electrodes in n trials under a first condition and m trials under a second condition;

acquires (n+m) response matrices from the measured brain electrical activity of the n and m trials;

performs canonical correlation analysis on response matrices included in the acquired (n+m) response matrices to obtain first canonical variable time series for the response matrices;

calculates a distance between the n and m trials for the response matrices from the obtained first canonical variable time series; and obtains a possibility that the n trials and the m trials are classified into two different clusters from the calculated distance and determines whether the first condition and the second condition are different or not by comparing the possibility with a specific value, and wherein brain electrical activity at D points of the target person is measured, with the D electrodes respectively, T times in the n trials 1, 2, ..., n and in the m trials n+1, n+2, ..., n+m, for each of an integer i (i=1, 2, ..., n, n+1, n+2, ..., n+m), an integer p (p=1, 2, ..., D), and an integer t (t=1, 2, ..., T), an element $X^{(i)}_p(t)$ in a row p and a column t of a response matrix $X^{(i)}$ obtained in the trial i is a value measured at a p-th point among the D points at a t-th sampling time since the the trial i starts, for each of the integer i (i=1, 2, ..., n, n+1, n+2, ..., n+m) and an integer j (j=1, 2, ..., n, n+1, n+2, ..., n+m), canonical correlation analysis is performed on the response matrix $X^{(i)}$ for the trial i and the response matrix $X^{(j)}$ for the trial j to obtain a first canonical variable time series $u_{i,j}$ for the response matrix $X^{(i)}$ and a first canonical variable time series $v_{i,j}$ for the response matrix $X^{(j)}$, and for each of the integer i (i=1, 2, ..., n, n+1, n+2, ..., n+m) and the integer j (j=1, 2, ..., n, n+1, n+2, ..., n+m), an element $S_{i,j}$ in a row i and a column j of a distance matrix S is assumed to be a distance between the trial i and the trial j that is calculated from the first canonical variable time series $u_{i,j}$ and the first canonical variable time series $v_{i,j}$, and wherein the possibility is obtained from the distance matrix S by:

placing the n and m trials 1, 2, ..., n, n+1, n+2, ..., n+m in a low-dimensional space by multidimensional scaling and applying a support vector machine and leave-one-out cross-validation to the n and m trials 1, 2, ..., n, n+1, n+2, ..., n+m placed in the low-dimensional space;

placing the n and m trials 1, 2, ..., n, n+1, n+2, ..., n+m in a low-dimensional space from the distance matrix S by multidimensional scaling and measuring overlap between a distribution of the n trials and a distribution of the m trials in the low-dimensional space; or creating from the distance matrix S a dendrogram in which the n and m trials 1, 2, ..., n, n+1, n+2, ..., n+m are clustered by hierarchical clustering measuring placement of the n trials and placement of the m trials in the dendrogram.

12. A non-transitory computer-readable information recording medium storing a program causing at least one processor included in a computer associated with D electrodes to:

measure brain electrical activity of a target person with the D electrodes in n trials under a first condition and m trials under a second condition;

acquire (n+m) response matrices from the measured brain electrical activity of the n and m trials;

perform canonical correlation analysis on response matrices included in the acquired (n+m) response matrices to obtain first canonical variable time series for the response matrices;

calculate a distance between the n and m trials for the response matrices from the obtained first canonical variable time series; and obtain a possibility that the n trials and the m trials are classified into two different clusters from the calculated distance and determines whether the first condition and the second condition are different or not by comparing the possibility with a specific value, and wherein brain electrical activity at D points of the target person is measured, with the D electrodes respectively, T times in the n trials 1, 2, ..., n and in the m trials n+1, n+2, ..., n+m, for each of an integer i (i=1, 2, ..., n, n+1, n+2, ..., n+m), an integer p (p=1, 2, ..., D), and an integer t (t=1, 2, ..., T), an element $X^{(i)}_p(t)$ in a row p and a column t of a response matrix $X^{(i)}$ obtained in the trial i is a value measured at a p-th point among the D points at a t-th sampling time since the trial i starts, for each of the integer i (i=1, 2, ..., n, n+1, n+2, ..., n+m) and an integer j (j=1, 2, ..., n, n+1, n+2, ..., n+m), canonical correlation analysis is performed on the response matrix $X^{(i)}$ for the trial i and the response matrix $X^{(j)}$ for the trial j to obtain a first canonical variable time series $u_{i,j}$ for the response matrix $X^{(i)}$ and a first canonical variable time series $v_{i,j}$ for the response matrix $X^{(j)}$, and for each of the integer i (i=1, 2, ..., n, n+1, n+2, ..., n+m) and the integer j (j=1, 2, ..., n, n+1, n+2, ..., n+m), an element $S_{i,j}$ in a row i and a column j of a distance matrix S is assumed to be a distance between the trial i and the trial j that is calculated from the first canonical variable time series $u_{i,j}$ and the first canonical variable time series $v_{i,j}$, and wherein the possibility is obtained from the distance matrix S by:

placing the n and m trials 1, 2, ..., n, n+1, n+2, ..., n+m in a low-dimensional space by multidimensional scaling and applying a support vector machine and leave-one-out cross-validation to the n and m trials 1, 2, ..., n, n+1, n+2, ..., n+m placed in the low-dimensional space;

placing the n and m trials 1, 2, ..., n, n+1, n+2, ..., n+m in a low-dimensional space from the distance matrix S by multidimensional scaling and measuring overlap between a distribution of the n trials and a distribution of the m trials in the low-dimensional space; or creating from the distance matrix S a dendrogram in which the n and m trials 1, 2, ..., n, n+1, n+2, ..., n+m are clustered by hierarchical clustering measuring placement of the n trials and placement of the m trials in the dendrogram.

* * * * *